United States Patent [19]

Rademacher et al.

[11] Patent Number: 5,212,298

[45] Date of Patent: May 18, 1993

[54] METHOD FOR PRODUCING SYNTHETIC N-LINKED GLYCOCONJUGATES

[75] Inventors: Thomas W. Rademacher; Ian D. Manger; Simon Wong; Raymond A. Dwek, all of Oxford, United Kingdom

[73] Assignee: Monsanto Company, St. Louis, Mo.

[21] Appl. No.: 776,911

[22] Filed: Oct. 15, 1991

Related U.S. Application Data

[63] Continuation-in-part of Ser. No. 394,691, Aug. 16, 1989, abandoned.

[51] Int. Cl.$^5$ .......... C07H 5/04; C07H 37/00
[52] U.S. Cl. .................. 536/55.2; 536/55.3; 536/53; 435/7.92
[58] Field of Search ........... 435/7; 536/53, 55.2, 536/55.3

[56] References Cited

FOREIGN PATENT DOCUMENTS

88/04323 6/1988 PCT Int'l Appl. .

OTHER PUBLICATIONS

Mota et al., Carbohyd. Res. 188, 35-44 (1989).
Stowell & Lee, Adv. Carbohydr. Chem. & Biochem. 37, 225-279 (1980).
Cheronis & Spitzmueller, J. Amer. Chem. Soc. 61, 349-375 (1941).
Garg & Jeanloz, Adv. Carbohyd. Chem. & Biochem. 43, 135-193 (1985).
Cowley et al., Carbohydr. Res. 19, 231-241 (1971).
Nakabayashi et al., Ibid. 174, 279-289 (1988).
Isbell & Frush, J. Org. Chem. 23, 1309-1319 (1958).
Frush & Isbell, J. Res. Natl. Bur. Stds. 47(4), 239-247 (1951).
Likhosherstov et al., Carbohydr. Res. 146, 61-65 (1986).
Thomas, "Carbohydrate Binding Sites" 1977, Meth. Enzymol. XLVI, No. 39, pp. 362-365.
Thomas, J. Med. Chem. 13(4), 755-756 (1970).
I. D. Manger, et al., Biochem. 31: 10724-10732, 1992.
I. D. Manger, et al., Biochem. 31: 10733-10740, 1992.

*Primary Examiner*—John W. Rollins
*Attorney, Agent, or Firm*—Scott J. Meyer

[57] ABSTRACT

A method is disclosed for derivatizing oligosaccharides to form synthetic N-linked glycoconjugates by converting a glycosylamine derivative of the oligosaccharide to a haloacetylated derivative as an intermediate compound prior to formation of the synthetic N-linked glycoconjugate to thereby directly maintain the $\beta$-anomeric configuration of said N-linked glycoconjugate.

21 Claims, 17 Drawing Sheets

METHOD FOR PRODUCING SYNTHETIC N-LINKED GLYCOCONJUGATES

CROSS-REFERENCE TO RELATED APPLICATION

This is a continuation-in-part of copending application Ser. No. 07/394,691, filed Aug. 16, 1989, now abandoned.

BACKGROUND OF THE INVENTION

This invention relates to a method for the derivitization of oligosaccharides to form synthetic N-linked glycoconjugates under conditions that maintain the β-anomeric configuration.

In general, carbohydrates are attached to various conjugates (e.g., proteins and lipids) by either N(nitrogen)-glycosidic or O(oxygen)-glycosidic linkages. Most animal glycoproteins contain oligosaccharides that are linked to a polypeptide backbone by a N-glycosidic linkage between N-acetyl-glucosamine (GlcNAc) and asparagine (Asn). The nitrogen glycosidic linkage between the reducing terminal monosaccharide (pyranose form) and asparagine in glycoproteins is in the β-anomeric configuration as shown by Formula I, below.

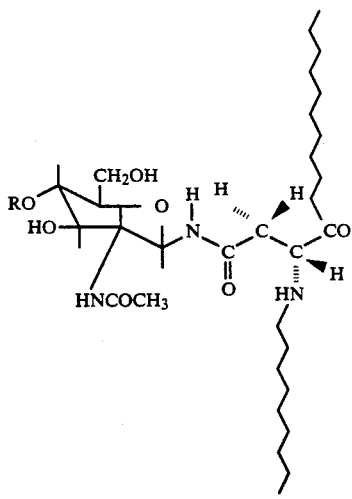

N-GLYCOSIDIC LINKAGE TO PROTEIN

Oligosaccharides with a free reducing terminus can be isolated from a variety of plant and animal sources. In addition, oligosaccharides can be released from glycoproteins by chemical or enzymatic methods. These saccharides also have a reducing terminal monosaccharide residue, typically GlcNAc or GalNAc (N-acetyl-galactosamine).

Derivatives of these oligosaccharides are useful in basic research activities concerning the function of the carbohydrate moieties of naturally occurring glycoconjugates, in clinical research and diagnostic medicine and in clinical pharmacology and therapeutics. The following list illustrates these useful derivatives.

1) Biotin conjugates of oligosaccharides.
2) Fluorescent conjugates of oligosaccharides.
3) Lipid conjugates of oligosaccharides.
4) Peptide conjugates of oligosaccharides.
5) Amino-acid conjugates of oligosaccharides.
6) Immobilized oligosaccharide to solid support (e.g. agarose gel columns, silicon chips, Petri dishes etc.).
7) Drug conjugates of oligosaccharides.
8) Chromophore conjugates of oligosaccharides.
9) 1-N-Protected glycosylamine derivatives, e.g. with carbobenzoxy (CBZ) or 9-fluorenylmethoxycarbonyl (FMOC) protecting groups.

Glycosylamines also are valuable intermediates in the synthesis of N-nucleosides, glycosylthioureas and glycosylamino heterocycles of biological and pharmaceutical interest. See, e.g., *Carbohydr. Res.* 188, 35–44 (1989), and references cited therein.

It would be desirable to make these oligosaccharide derivatives such that the linkage between the asparagine and the reducing terminal GlcNAc (i.e. GlcNAc→Asn) which occurs in glycoproteins as in Formula I is preserved. That is, it would be desirable to maintain the β-anomeric configuration, pyranose form and carbonyl and methylene components of the asparagine. Formula II illustrates the nature of the GlcNAc→Asn linkage in glycoproteins; Formula III shows the chemical form of illustrative derivatives which thus would preserve the characteristics of the GlcNAc→Asn linkage.

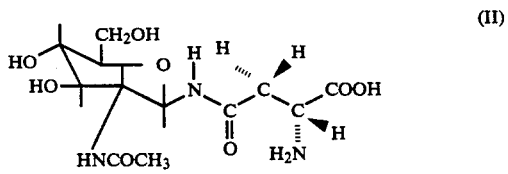

2-ACETAMIDO-1-N(4'-L-ASPARTYL)2-DEOXY-β-D-GLUCOPYRANOSYLAMINE
(GlcNAc—Asn)

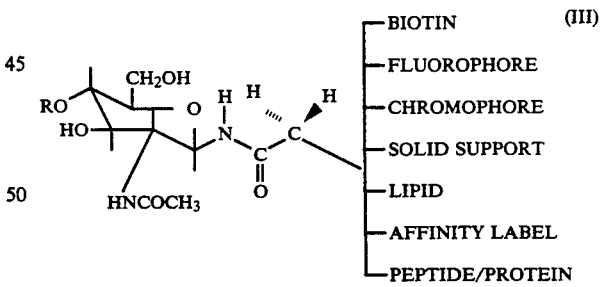

A number of published methods for derivatizing oligosaccharides are available but they do not preserve all the aforesaid desired characteristics of the GlcNAc→Asn linkage.

One prior method of oligosaccharide derivatization involves reductive amination as described, for example, by Stowell and Lee, *Adv. Carbohydr. Chem. and Biochem.* 37, 225–279 (1980), especially pg. 245. However, the described techniques do not preserve the pyranose form and the anomeric centre of the reducing terminal monosaccharide, nor the carbonyl and methylene groups of asparagine as can be seen from the following two illustrative reaction schemes:

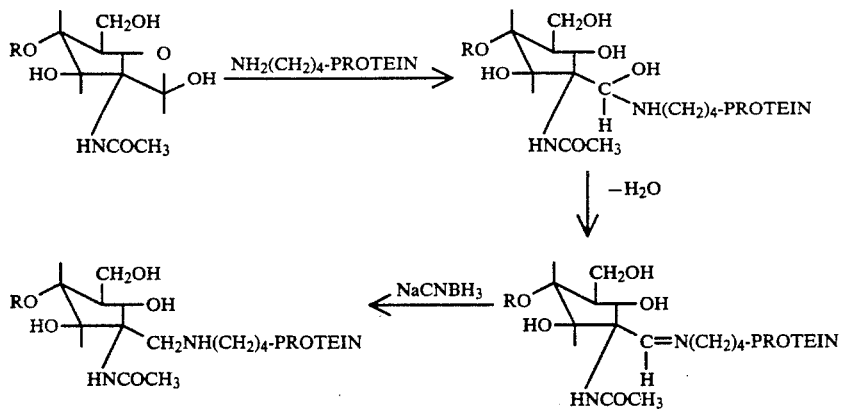

NEOGLYCOPROTEIN FORMATION BY REDUCTIVE AMINATION

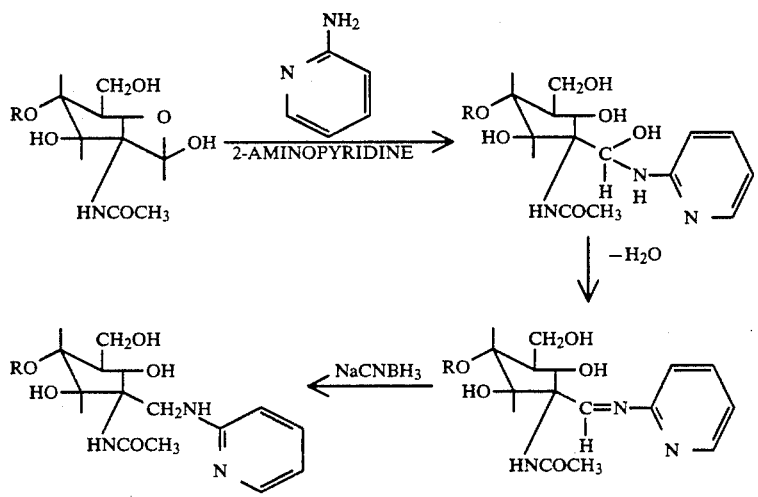

FLUORESCENT DERIVATIZATION BY REDUCTIVE AMINATION

Another prior method of oligosaccharide derivatization involves formation of glycoconjugates by direct derivatization of glycosylamines as illustrated in PCT Inter. Pat. Appln. WO 88/04323, published Jun. 16, 1988. Although these techniques preserve the pyranose form of the reducing GlcNAc, they do not necessarily preserve the β-anomeric configuration (a mixture of products is obtained) nor the carbonyl and methylene group of the asparagine as seen from the following illustrative product formula IV. Moreover, the methodology is applicable only to N-linked oligosaccharides attached to glycoproteins and, thereby, is of limited use.

(IV)

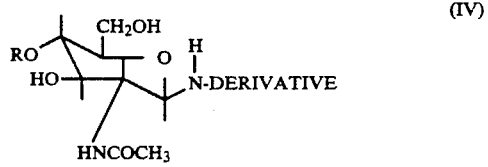

FORMATION OF GLYCOCONJUGATES
BY DIRECT DERIVATIZATION OF
GLYCOSYLAMINES

BRIEF DESCRIPTION OF THE INVENTION

In accordance with the present invention, a novel method is provided for the derivatization of oligosaccharides to form synthetic N-linked glycoconjugates under conditions that maintain the β-anomeric configuration. It has been found that the β-anomeric configuration can thus be substantially preserved by converting a glycosylamine derivative of said oligosaccharide to a haloacetylated derivative as an intermediate compound prior to formation of the desired N-linked glycoconjugate. Preferably, the haloacetylated derivative is a chloroacetylated derivative. Conversion of the glycosylamine to a haloacetylated derivative can be carried out by reaction with a reagent capable of donating a haloacetyl function to the glycosylamine. In accordance with the invention, any reducing monosaccharide or polysaccharide with a reducing monosaccharide can be thus derivatized.

In accordance with another preferred aspect of the invention, the oligosaccharide derivatization is employed in an overall three step method as follows:

1) Synthesis of a glycosylamine derivative of the oligosaccharide such that the pyranose form and the β-configuration of the reducing terminal monosaccharide (usually GlcNAc) is preserved.

2) Synthesis of a haloacetylated derivative of the glycosylamine. This synthetic step must not involve mutarotation of the β-configuration of the glycosylamine.

3) Conversion of the haloacetylated derivative to either a synthetically useful intermediate or direct derivatization of the haloacetylated glycosylamine with a conjugate.

In the method of the invention, the haloacetylation is preferably carried out by reaction of the glycosylamine with an excess of chloroacetic anhydride (also referred to as svm. dichloroacetic anhydride). In the case of the bromo- and iodo-derivatives, the NHS-ester of the acid can be used, e.g. N-(iodoacetyloxy)succinimide (ICH$_2$COONHS). Preferably, a molar excess of at least about 5-fold, e.g. 5- to 10-fold, of the N-acetylation reagent is thus used. Use of the chloroacetic anhydride surprisingly results in an intermediate which remains about 98% in the β-anomeric configuration compared to prior art methods, e.g. dansyl chloride, which result in mixtures with significant amounts of α-anomeric product. Although chloroacetic anhydride is a known reagent for the N-acetylation of amino acids, and ammonolysis of halogen fatty acids to prepare α-amino acids is known [Cheronis and Spitzmueller, *J. Amer. Chem. Soc.* 61, 349-375 (1941)], its high N-specific reactivity with the glycosylamine and the retention of the β-anomeric configuration in the formation of N-linked oligosaccharides as described herein were unexpected. Thus, the steps of separating the α- and β-anomeric configurations are unnecessary such as is frequently required with the simple sugars which tend to mutarotate. Selective crystallization in organic solvent medium such as used in the case of the simple sugars is not adaptable to the oligosaccharides since they tend to form glasses rather than crystals, and complex oligosaccharides are not generally soluble in organic solvents but need to be reacted in aqueous medium. As defined herein, the oligosaccharides preferably contain from 3 to 20 saccharide units per molecule.

In the overall three step method, the initial glycosylation of the oligosaccharide is preferably carried out by incubation of the oligosaccharide in saturated ammonium bicarbonate at moderate alkaline pH of about 8-8.5, and preferably at about pH 8.3. Glycosylation under these conditions results in a glycosylamine in the β-anomeric configuration.

Following the haloacetylation reaction as described above, the desired haloacetylated glycosylamine intermediate can be used to synthesize a variety of N-glycyl-β-glycosylamines or N-linked glycoconjugates as described hereinbefore and shown in Formula III. For example, a fluorescent conjugate of the oligosaccharide can be made by reaction of the N-glycyl-β-glycosylamine intermediate with a fluorophore such as a fluorescein or rhodamine derivative. Similar reaction with a chromophore, e.g. p-nitrophenylalanine, can be carried out to produce a chromophoric conjugate of the oligosaccharide. A lipid conjugate of the oligosaccharide can be made by reaction of the N-glycyl-β-glycosylamine intermediate with a lipopeptide carrier (following activation with thiophosgene) such as, e.g., P$_3$C (tripalmitoyl-S-glycerylcysteine). An example of a peptide conjugate of the oligosaccharide can be prepared by either direct coupling reaction of the β-glycosylamine or the N-glycyl-β-glycosylamine intermediate derivative to a suitable peptide having an activated carboxyl group, e.g., an atriopeptin, to produce a neoglycohormone.

Also illustratively, a protein conjugate of the intermediate can be synthesized by coupling to a protein such as, e.g., gentiobiose/human serum albumin, to produce a neoglycoprotein. Conjugation of the oligosaccharide with a solid support is exemplified by coupling to a plastic surface, e.g., a plastic tissue culture plate such as polystyrene or a protein-coated plastic surface.

Although specific illustrative substrates capable of forming a 1-N-glycyl-β-glycosylamine linked glycoconjugate with the 1-N-glycyl-β-glycosylamine derivatives of oligosaccharides are described herein, it will be understood that the invention is not limited to the use of these specific substrates.

Use of the haloacetyl donating reagent to form the intermediate haloacetylated derivative of the glycosylamine prior to formation of the glycoconjugate is critical to the invention. It has been found that direct derivatization of the glycosylamine such as by use of a trapping agent such as acid chlorides, acid anhydrides and other active acyl compounds as disclosed in PCT Inter. Appln. WO 88/04323 is not a practical method to produce glycoconjugates in high yield in the β-anomeric form. Also, acid chlorides will react with the hydroxy group of the sugar, i.e. it is not an N-specific derivatization reagent, and acetic anhydride forms a synthetically useless derivative of the glycosylamine.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in conjunction with the appended drawings, in which:

In each, after 4 days, the amount of incorporated $^3$H-thymidine (cmp) was measured. A decrease in the cpm indicates an inhibition of lymphocyte proliferation.

Figure 16A:
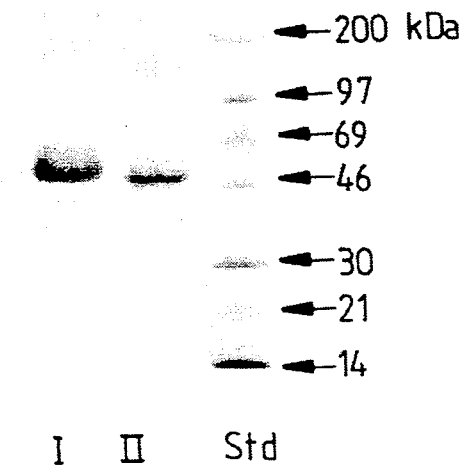

FIG. 16A shows the SDS PAGE of the neoglycoprotein derivatives of BSA and N'N'-diacetylchitobiose.

Figure 16B:
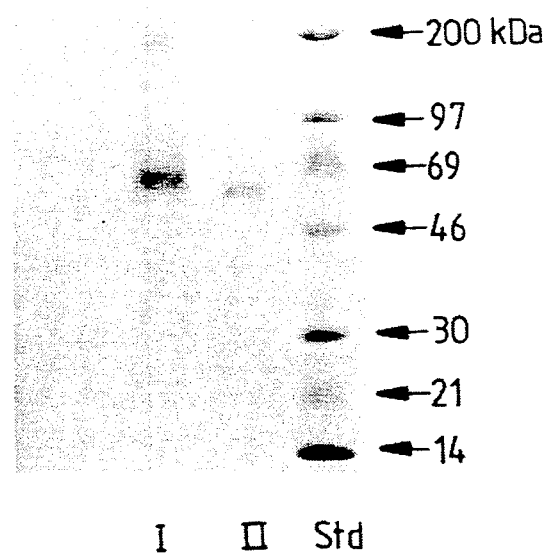

FIG. 16B shows the SDS PAGE of the neoglycoprotein derivatives of BSA and 5.8 sugar.

Lane AI, BSA-(GlcNAc$\beta$4GlcNAc)$_{16}$: AII, BSA prederivatization: BI, BSA-(5,8)$_{13}$: BII, BSA prederivatization. Std—standard m.w. markers.

Figure 17:
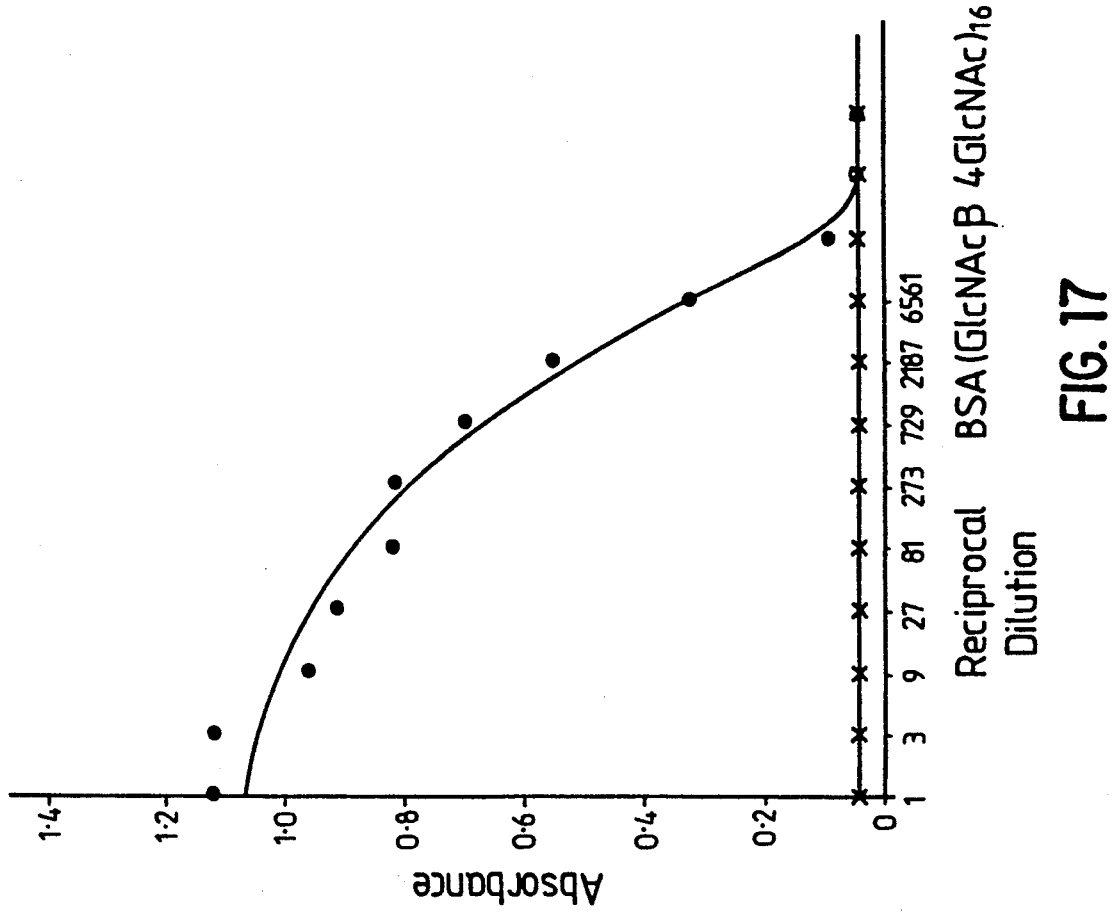

FIG. 17 is a graphical representation which shows the binding of an IgM anti-GlcNAc antibody (GN7) to a neoglycoprotein derivatized petri dish.

It will be appreciated that the oligosaccharides used in the method of the invention can be isolated or derived from a variety of plant and animal materials such as, for example:

(1) Purified glycoproteins and glycohormones;
(2) Whole serum and its fractions;
(3) Biological secretions such as, for example, urine, milk, meconium, mucus, colostrum and the like substances;
(4) Whole organs, for example, kidneys, liver, heart, spleen, pancreas, lung;
(5) Plant stem and leaf extracts;
(6) Seed material;
(7) Lectins; and
(8) Emulsins.

Release of oligosaccharides from such plant and animal material by chemical means such as hydrazinolysis is described in U.S. Pat. Nos. 4,719,294 and 4,736,022 and by Takasaki et al., *Meth. Enzymol.* 83, 263–268 (1982).

Release of oligosaccharides by enzymatic methods is illustrated by the use of N-glycanase as described by Hirani et al., *Anal. Biochem.* 162, 485–492 (1987).

The derivatization of the oligosaccharides to form synthetic N-linked glycoconjugates under conditions that maintain the $\beta$-anomeric configuration is illustrated hereinafter in detail by the overall three step method.

STEP 1. FORMATION OF GLYCOSYLAMINES

Prior to the present invention, no adequate general method existed for the synthesis of glycosylamines.

The following methods have previously been described.

1. A method for producing glycosylamines via a glycosyl azide [Garg and Jeanloz, *Adv. Carbohyd. Chem. and Biochem.* 43, 135–139 (1985); Cowley et al., *Carbohydr. Res.* 19, 231–241 (1971); and Nakabayashi et al., Ibid. 174, 279–289 (1988)].

2. A method for producing glycosylamines using methanolic ammonia [Frush and Isbell, *J. Org. Chem.* 23, 1309 (1958); Frush and Isbell, *J. Res. Natl. Bur. Stds.* 47 (4), 239–247 (1951)]. This method is not applicable to larger structures owing to their insolubility in this solvent system, and the susceptibility of reducing terminal N-acetylglucosamine residues to undergo base catalyzed epimerization at C2, or to $\beta$-elimination of 1–3 linked core fucose.

3. A one step condensation of a saccharide and ammonia using saturated ammonium bicarbonate [Likhosherstov et al., *Carbohydr. Res.* 146, C1–C5 (1986)].

4. Enzymatic methods whereby glycoproteins are reacted with a $\beta$-aspartyl glycosylamine amidohydrolase (PCT Inter. Pat. Appln. WO 88/04323).

A modification of the general ammonium bicarbonate procedure is used herein. The formation of glycosylamines by the condensation of monosaccharides and ammonia has been extensively studied by Frush and Isbell as noted above. The reaction is thought to proceed via the acyclic ammonium ion (Schiff adduct) followed by recyclization to give the glycosylamine. The method of Likhosherstov et al. uses ammonium bicarbonate as the ammonia source rather than the methanolic ammonia used by Isbell and Frush. This method has the advantages that larger oligosaccharides may be soluble in this aqueous system. While ammonium salts may increase the formation of bisglycosylamines by the splitting out of ammonia between two glycosylamine molecules, low concentrations of sugar minimize this side reaction.

Glycosylamines undergo rapid ring opening rearrangements and the outcome of these is strongly dependent on the pH. Above pH 8.0 they mutarotate rapidly with the equilibrium in favor of the β-form as shown by Isbell and Frush, *J. Org. Chem.* 23, 309 (1958) (see FIG. 1). Glycosylamines are readily hydrolyzed at moderately acidic pH (~4.5) (see FIG. 1). As a consequence of these chemical properties, any work-up procedure and subsequent synthetic reactions must be adequately buffered to balance general acid catalyzed hydrolysis (by a reverse of the reaction sequence shown in FIG. 1) and to maintain the amine as a reactive nucleophile (i.e. deprotonated).

The formation of glycosylamines and the yield obtained is therefore dependent on the use of moderate basic conditions which minimize side reactions of the starting sugar, and avoidance of acidic conditions which catalyze hydrolysis of the amine. Further, the possibility of base catalyzed epimerization at C2 and β-elinination occurring can be minimized if the reaction occurs at moderately alkaline pH of about 8-8.5 and preferably about 8.3.

A summary of the general ammonium bicarbonate method of Likhosherstov et al. is shown by the following reaction scheme:

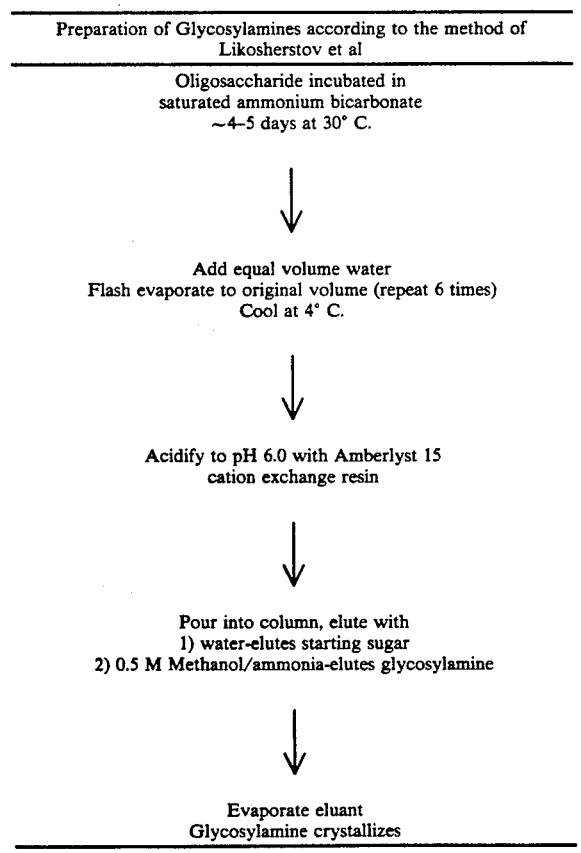

Preparation of Glycosylamines according to the method of Likosherstov et al

Oligosaccharide incubated in
saturated ammonium bicarbonate
~4–5 days at 30° C.

↓

Add equal volume water
Flash evaporate to original volume (repeat 6 times)
Cool at 4° C.

↓

Acidify to pH 6.0 with Amberlyst 15
cation exchange resin

↓

Pour into column, elute with
1) water-elutes starting sugar
2) 0.5 M Methanol/ammonia-elutes glycosylamine

↓

Evaporate eluant
Glycosylamine crystallizes

The authors claim that this method is effective in producing glycosylamines of simple mono- and disaccharides in 60% yield. However, the present inventors have not been able to duplicate their yields using the published procedure. The following observations were made.

Figure 1:
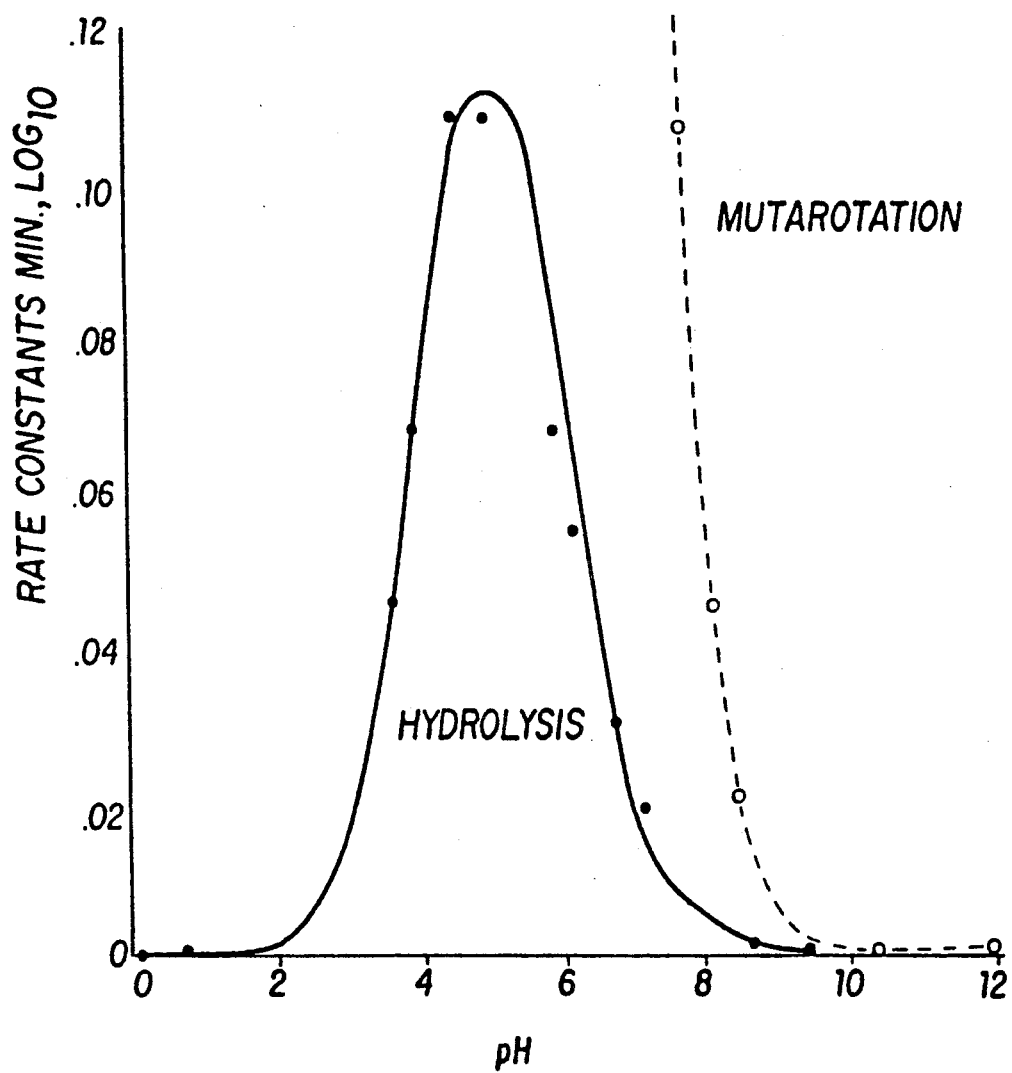
FIG. 1 is a graphical representation which shows the pH dependence of mutarotation and hydrolysis of glycosylamines.

1) The acidification of the reaction mixture must be very carefully controlled, since the hydrolysis of the glycosylamine is most rapid at moderately acidic pH (see FIG. 1). This step is difficult to control with a small oligosaccharide sample (analytic scale).

2) The Amberlyst exchange resin used is unstable in the methanolic ammonia eluant. Despite extensive washings the resin was solubilized and appeared as a discolorant. Further investigation of the properties of the Amerlyst resin (see Experiments below) also showed that it was not possible to quantitatively elute glycosylamines under the published conditions. Another resin, AG50×12(H+) was tested, but it also bound the glycosylamine strongly at acidic pH. The simple glycosylamine of N-acetylglucosamine could not be quantitatively eluted from columns of this resin.

Experimental

Acidification of saturated ammonium bicarbonate was performed according to the method of Likkosherstov et al. Since hydrolysis is most rapid at mildly acidic pH (see above), this was carefully controlled.

For elution experiments, 200 μl (560 μEq) of saturated ammonium bicarbonate containing $^3$H-GlcNAc was incubated for 4 days at 30° C. and then applied to a column of 400 μl (600 μEq) Amberlyst resin which had previously been extensively washed with 10 column volumes 1M HCl, 10 column volumes of 0.5M MeOH/NH$_3$ and then with 20 column volumes of water. Unbound sugar (free N-acetylglucosamine) was eluted by 10 column volumes of water, evaporated to dryness and counted. Bound glycosylamine was eluted using various concentrations of ammonia/methanol as indicated in Table I. The eluants were dried and counted.

Table I shows the amount of bound monosaccharide eluted from the resin using these eluants. From these data it is evident that a large fraction of the amine remains strongly bound to the resin. The nature of this interaction is unknown.

TABLE I

| Elution of $^3$H—N-acetylglucosamine from Amberlyst 15 resin | | |
|---|---|---|
| Eluant | % Bound | % Free |
| Water | 83.5% | 15.5% |
| 0.5 M | 71.4%* | |
| 1.0 M | 50.8%* | |
| 2.0 M | 39.9%* | |
| 4.0 M | 36.0%* | |

*Percent of material not eluted by water

These problems prompted the present inventors to develop other methods of isolation which can be generally applied to oligosaccharide glycosylamines (both analytic and preparative).

Removal of Ammonia During Glycosylamine Synthesis

The complete removal of the ammonium bicarbonate from the mixture is a major problem. From the results above, quantitative recovery of the glycosylamine from ion-exchange resins is not believed to be possible. Desalting of larger glycosylamines may be simply achieved by using gel filtration chromatography eluted with water, but associated problems generally occur as follows:
1) hydrolysis of the glycosylamine in water.
2) oligosaccharides can interact with the column matrix giving rise to non-quantitative recoveries.

The present inventors found that significant amounts of the ammonium salts may be removed without hydrolysis of the glycosylamine, by the addition of methanol to approximately 90% by volume. This decreases the solubility of the salt from 220 mg/ml (20° C.) to about 0.01 mg/ml. The precipitated salts can be filtered off and washed to recover any surface bound sugar. Remaining salts can be can be removed by lyophilization. In practice, it was found that small oligosaccharide samples can be lyophilized directly from the reaction mixture.

EXAMPLE 1

Figure 2:
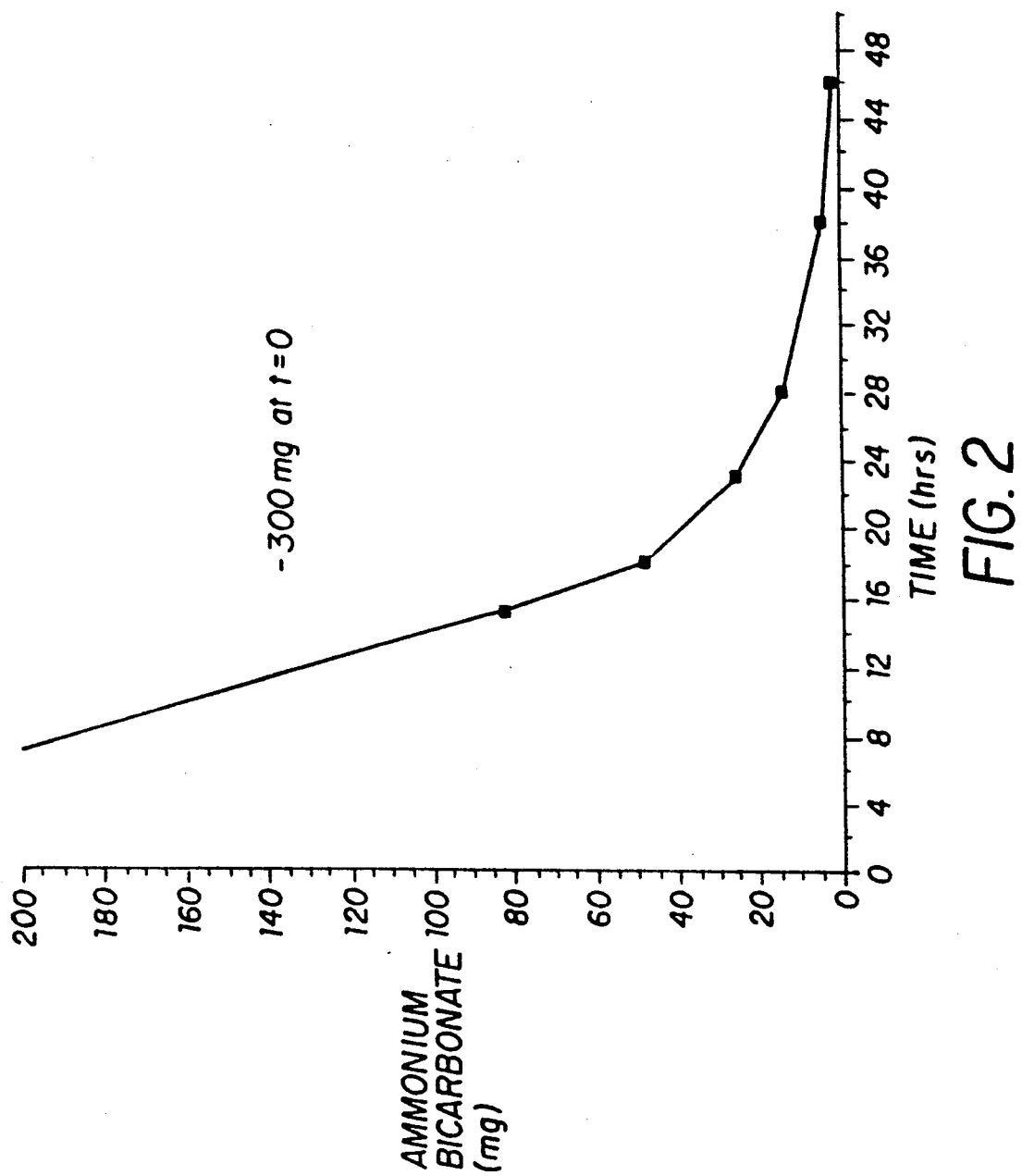
FIG. 2 is a graphical representation which shows the removal of ammonium bicarbonate from oligosaccharides with time during lyophilization.
Figure 3:
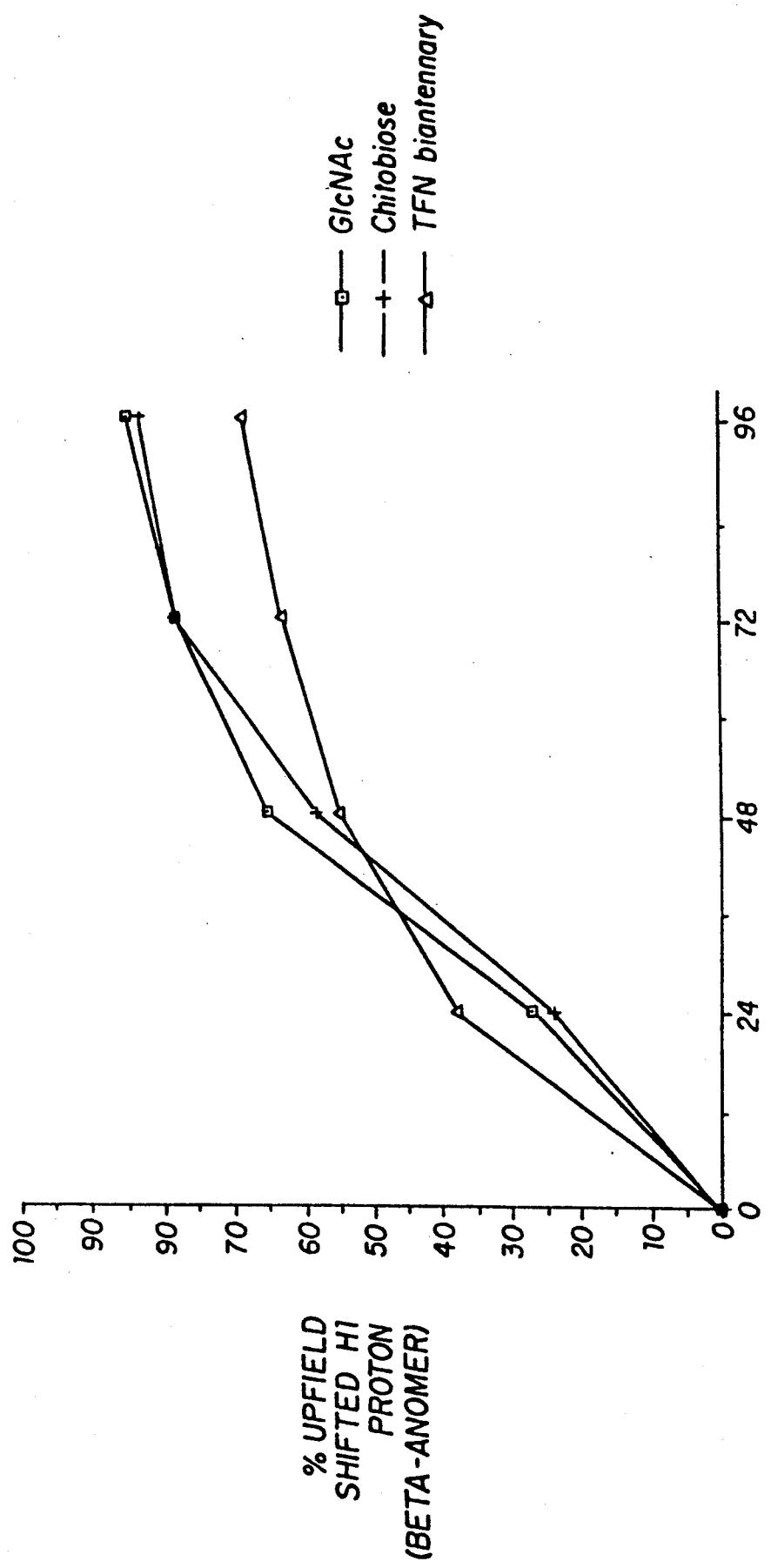
FIG. 3 is a graphical representation which shows the rate of formation of glycosylamine during incubation of oligosaccharide in saturated ammonium bicarbonate in one embodiment of the invention.

Samples of oligosaccharide in saturated ammonium bicarbonate (typically 50–100 μl) were diluted to 1 ml and shell frozen in dry ice. These were then lyophilized at a chamber pressure of $10^3$ bar. FIG. 2 shows the removal of ammonium bicarbonate with time. In practice, the removal of ammonium bicarbonate can be accelerated by 6 hr repeat cycles of addition of water and lyophilization (data not shown). At the end of the lyophilization, samples are stored at −20° C. in the presence of dessicant. Under these conditions they were found to be stable over at least a one month period. The rate of their formation as determined by $^1$H-NMR Spectroscopy described below is shown in FIG. 3. Note that the glucosamines are in the pyranose form with an α/β anomer ratio of ∼1:24.

$^1$H-NMR spectra of glycosylamines

The formation of glycosylamine from the reducing sugar can be followed by $^1$H-NMR spectroscopy. The condensation of sugar with ammonia is indicated by the collapse of the anomeric protons of the free sugar, and the appearance of a major resonance associated with the β-anomer of the glycosylamine, which for steric reasons ($^4C_1$ configuration) is the more stable anomer. For N-acetylglucosamine the anomeric protons of the free sugar were found to resonate at 5.19 ppm (α) and 4.70 ppm (β), with associated $J_{1,2}$ values of ∼3.5 Hz and ∼8 Hz, respectively. The glycosylamine has a major resonance at 4.15 ppm, and from the $J_{1,2}$ value of ∼8 Hz, this can be identified as the β-anomer. Other minor components can also be identified, one of which is the α-anomer (4.39 ppm, $J_{1,2}$∼4.7 Hz) (α/β ratio 1:24).

Experimental

A sample of GlcNAc, GlcNAcβ1→4GlcNAc and Galβ1→4GlcNAcβ1→2Manα1→6[Galβ1→4GlcNAcβ1→2Manα1→3]Manβ1→4GlcNAcβ1→4GlcNAc was derivatized using ammonium bicarbonate, and at 24 hr time points samples were withdrawn and lyophilized. These were then exchanged into $D_2O$ (99.96 atom) and 1D-spectra obtained. Integrals of the anomeric region were taken, and by comparison with the methyl region the percentage of each species was obtained. The results obtained are shown in the FIG. 3. These data suggest that condensation of the sugar with ammonia is complete after 3–4 days at room temperature.

STEP. 2 HALOACETYLATION OF GLYCOSYLAMINES

Halocetylation was performed by reacting the glycosylamine with, for example, chloroacetic anhydride as illustrated by the following reaction scheme:

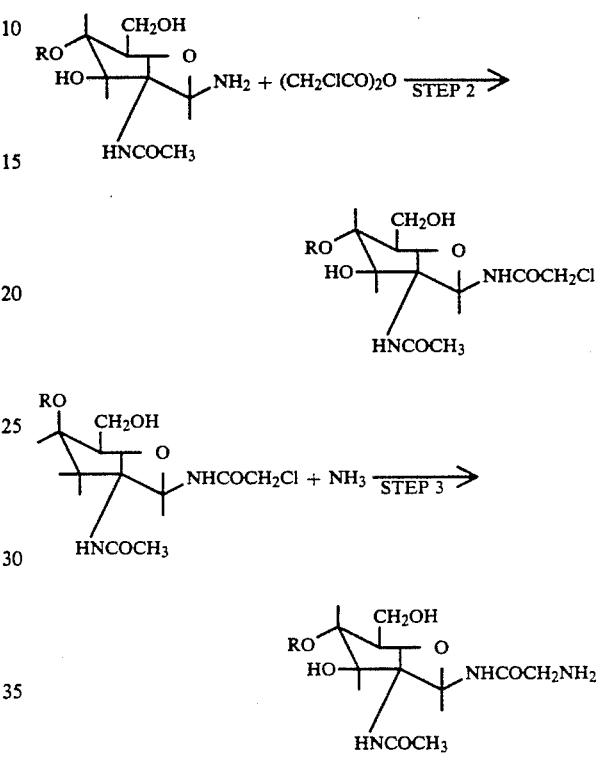

INTRODUCTION OF GLYCINE SPACER USING CHLOROACETYLATION

In the case of bromo- and iodo-derivatives the NHS-ester of the acid can be used as illustrated by the following reaction scheme using ICH$_2$COONHS:

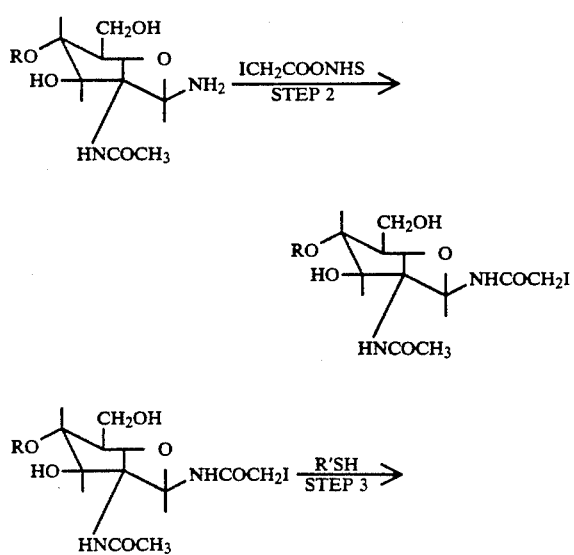

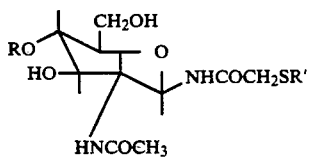

FORMATION OF
GLYCOCONJUGATES VIA THIOETHERS

EXAMPLE 2

Figure 4:
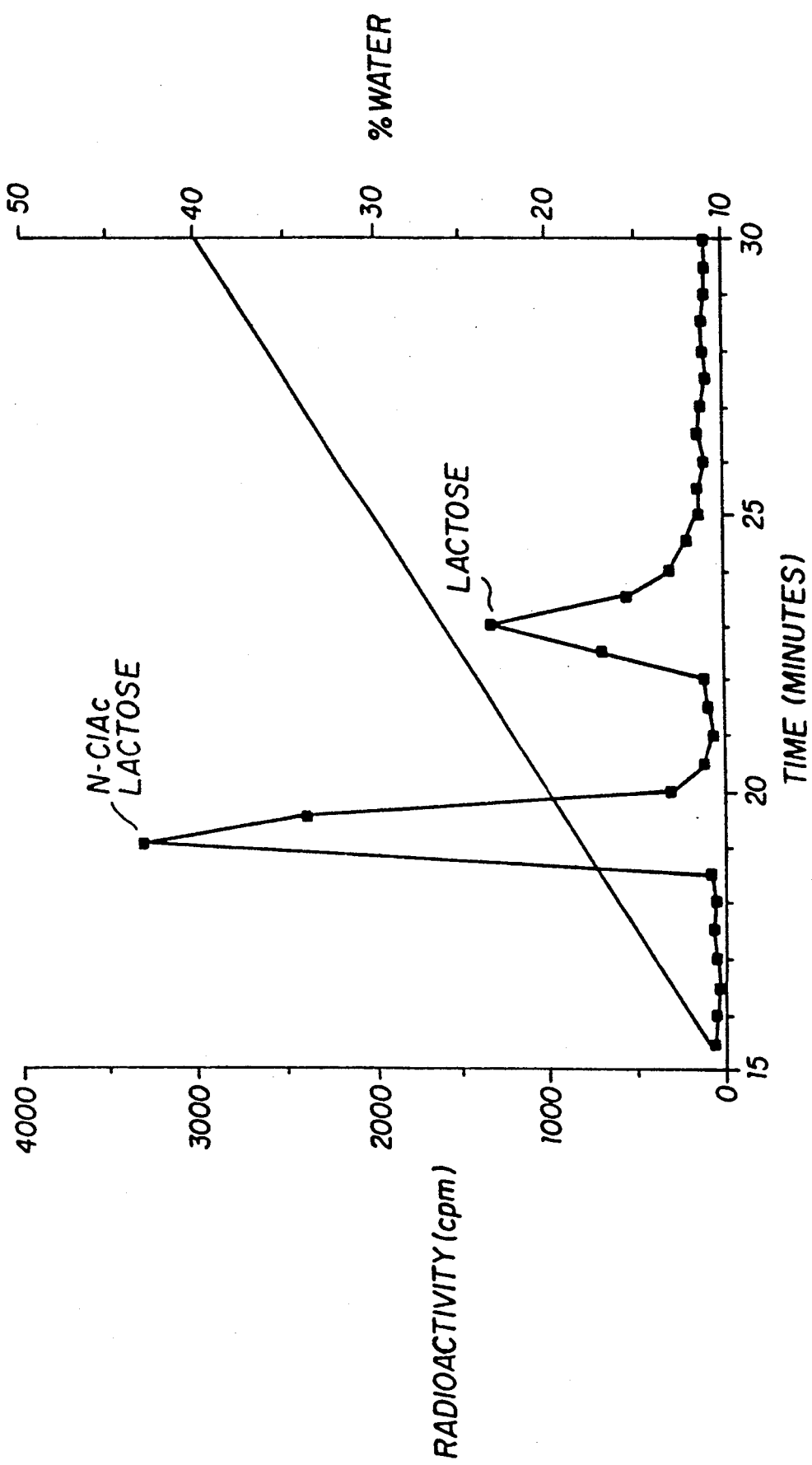
FIG. 4 is a graphical representation which shows the HPLC elution profile of product obtained by chloroacetylation of the glycosylamine of FIG. 3.

$^{14}$C-lactosylamine (0.32mCi/mmole) was made by condensation with ammonium bicarbonate. Following removal of the ammonium salts as described in Step 1, above, the sample was resuspended in 1.0M NaHCO$_3$ and chloroacetylated by the addition of a five-fold molar excess of sym. dichloroacetic-anhydride (Fluka Biochemicals). After a 2 hr. incubation at room temperature a second quantity of base and anhydride was added. After a further 6 hrs. the mixture was passed over a mixed bed of AG50-X12(H+) and AG3-X4A(OH−) ion exchange resins. The eluant was collected and evaporated to dryness. Separation of the reaction products was performed using ion-supression amine absorption HPLC according to the method of Mellis and Baenzinger, *Anal. Biochem.* 134, 442 (1984) The reaction products were resuspended in 90% MeCN/10% water containing 50 mM triethylamine acetate (TEA) buffer, pH 5.5, and injected onto a Varian Micropak AX5 column equilibrated in the same buffer. Elution was performed using a 2%/min. gradient of TEA buffer following a 5 min. hold at the equilibration conditions. Radioactive products were detected using a Berthold LB503 HPLC radioactivity monitor. A typical profile is shown in FIG. 4. Radioactive fractions were pooled and dried.

The characterization of the 1-amino chloroacetyl-glycosylamine by NMR analysis as described below showed that the glycosylamine was still predominantly in the β-anomer configuration α/β (1:24) post haloacetylation. This contrasts with direct derivatization of the glycosylamine with, for example, dansyl chloride, which resulted in muta-rotation, as shown below.

$^1$H-NMR analysis of N-chloroacetyl and N-acetyl-glycyl-derivatives of 1-amino-N-acetyl glucosamine.

A sample of 1-amino-N-acetylglucosamine was N-chloroacetylated. At the end of the incubation period, the mixture was passed over a mixed bed of AG50-X12 and AG3-X4A ion exchange resins. The eluant was then evaporated to dryness under reduced pressure and lyophilized. It was then twice-exchanged into D20 and subjected to 1-D $^1$H-NMR analysis. The spectrum obtained showed the presence of four distinct saccharide components in the anomeric region. These are the α- and β-forms of the free sugar and of N-chloroacetyl derivative. Inspection of the integrals for these four species gave an overall yield of ~75% for formation of the chloroacetyl derivative, in a ratio of 24:1 in favor of the β-anomer.

The mixture was then subjected to ammonolysis at 50° C. using an AG50x12-binding assay to follow the time course of the reaction. The glycyl-derivative was then purified on a short column of CM-Sepharose Fast Flow, eluted first with water and then with 0.5M ammonium carbonate. The material eluted by the salt was then pooled and the salt removed by evaporation. The mixture was then N-acetylated using acetic anhydride in saturated sodium bicarbonate and desalted using AG50/AG3 resins. The product was split into two for NMR analysis. One half was dried and redissolved in DMSO-d5 (Aldrich) and the other was exchanged into D20 and analyzed as described above.

A portion of the spectrum obtained in DMSO showed the downfield NH protons which are normally exchanged in D20. Two doublets at 7.84 and 7.88 ppm can be assigned as those of NH1 and NH2 on the basis of spin decoupling by irradiation at 4.55 ppm (triplet resonance of H1). The third resonance, a triplet at 8.09 ppm, was assigned to the NH of the "glycine" acetamido function. Irradiation of this resonance causes perturbation of resonances between 3.40 and 3.60 ppm which may assigned to the two methylene protons of the glycine space. Finally there are two well resolved methyl resonances at 1.70 and 1.80 ppm.

Reactivity of Glycosylamines (Dansyl and Fluorescein Derivatives)

The reaction between 1-amino-2-acetamido-1,2-dideoxy-D-glucopyranosyl-amine and dimethylaminonapthalenesulphonyl chloride (dansyl chloride) was performed by a modification of the method of Gray, *Meth. Enz. XXV,* 121, (1971). 10 μmole of the amine was dissolved in 200 μl of 0.5 M NaHCO$_3$. 200 μl of ethanol containing 24.5 mg dansyl chloride was then added with stirring and the reaction allowed to proceed at room temperature for 2 hrs. A brown solution containing some precipitated sodium bicarbonate was obtained. Following the addition of 100 μl of water to dissolve the precipitate, the products were separated using reverse phase chromatography on a Spherisorb S50DS2 SP column (8.0×300 mm), using UV (258 nm) and fluorescence detection (exit. 336 nm-emiss. 536 nm). Column fractions were collected and 50 μl aliquots counted. Pooled fractions containing radioactivity were then evaporated to dryness, resuspended in 1 ml water and counted to obtain the yield. Typical yields obtained by this method are 10–15% based on starting sugar.

The dansyl-aminosugar obtained by this method was lyophilized and then prepared for NMR analysis by twice exchanging into D$_2$O (99.96 atom) and finally redissolved in the same solvent. 1-D and 2-D analysis was performed using a Bruker 500 Hz spectrometer. A 1D spectrum of the derivative showed the characteristic downfield aromatic resonances and well resolved anomeric, backbone and acetamidomethyl regions. This derivative showed a 1:4 ratio of the α and β forms respectively, compared with the 1:24 ratio observed in the unreacted glycosylamine (see above). There are at least two possible explanations for this observation, firstly that the dansyl derivative is capable of undergoing mutarotation via the ring open form, or secondly that the α-form reacts more rapidly than the β-form with dansyl chloride and that once formed the derivative is fixed as a particular anomer. Temperature and pH dependent studies favor the latter interpretation (data not shown).

The generally poor yields obtained for dansyl chloride were found to be typical of the reactions of glycosylamines. For example, similar yields were obtained with the isothiocyanate and NHS-esters of fluorescein. Acid chlorides such as dansyl chloride present an added difficulty in that there is the likelihood of O-acylation with these highly reactive species. Indeed, this was found to be the case when the kinetics of dansylation with various glycosylamine was studied (data not shown). The formation of 0-dansyl derivatives represents a further route by which the acid chloride may be consumed.

It was therefore concluded that direct derivatization of glycosylamines results in α and β mixtures of the products and low yields were consistently found.

STEP 3. SYNTHESIS OF N-GLYCYL-β-GLYCOSYLAMINES

The haloacetylated glycosylamine derivatives can be used in a number of synthetic strategies. For example, the halo-function can be replaced by a primary amine, such as in the synthesis of glycine using chloroacetic acid, or iodo-derivatives can be linked to thiols to form thioethers as shown by reaction schemes hereinbefore.

EXAMPLE 3

Figure 5:
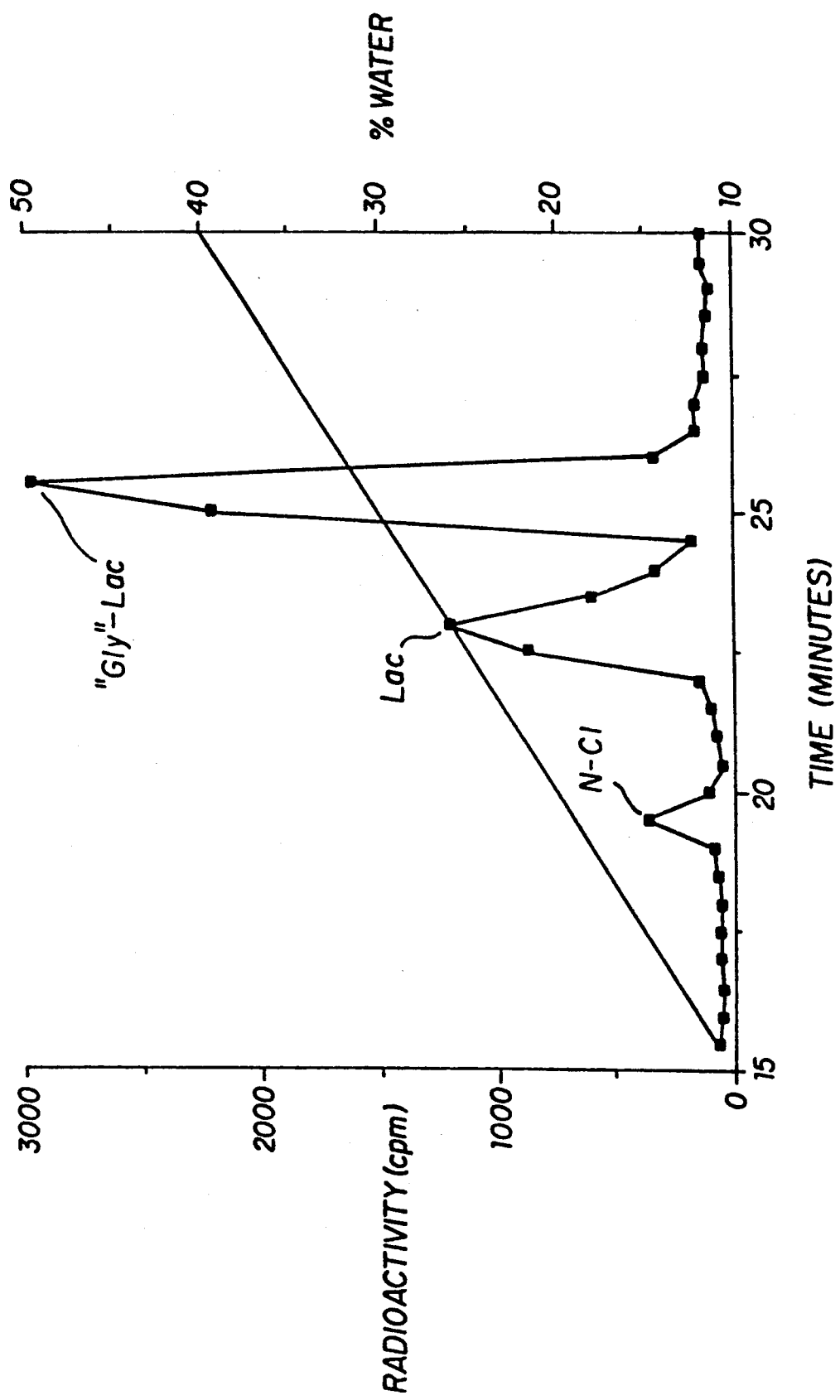
FIG. 5 is a graphical representation which shows the HPLC elution profile of products from the ammonolysis of the chloroacetylated glycosamine of FIG. 4.
Figure 6:
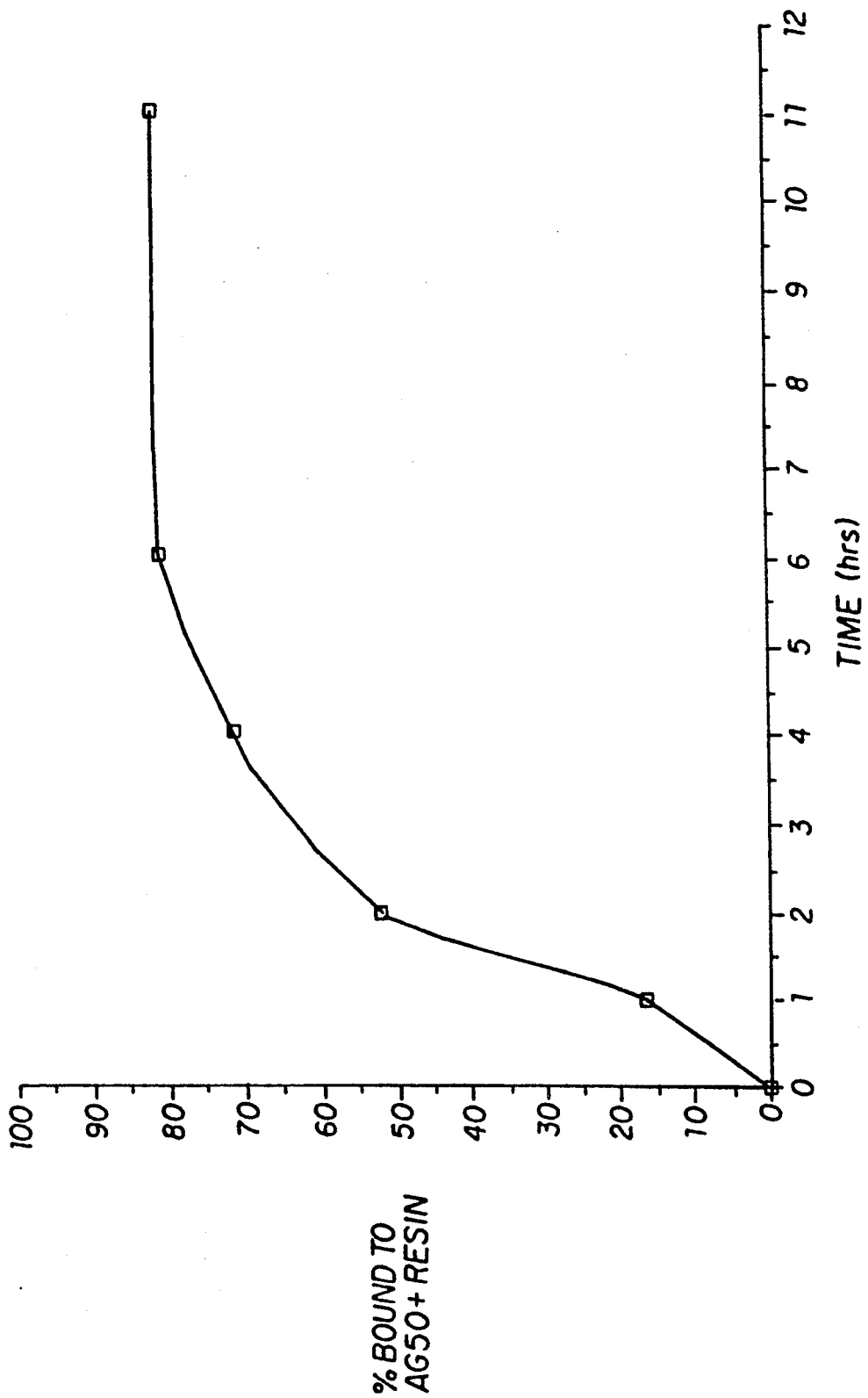
FIG. 6 is a graphical representation which shows the completion of a second ammonolysis reaction as in FIG. 5.

Ammonolysis of the haloacetate derivative was performed by incubation in saturated ammonium carbonate in a sealed tube (to prevent loss of ammonia by evaporation) at room temperature. The products were analyzed using the same HPLC method as above. In the reaction the chloroacetate derivative eluting at 18.8 minutes was converted slowly to a product eluting at ~24 min. which was ninhydrin sensitive (see FIG. 5). The reaction was essentially complete after 96 hrs. at room temperature (see FIG. 5). A second ammonolysis reaction was carried out at 50° C. and was found to be complete after overnight incubation. (see FIG. 6). An excess of ammonia over chloroacetyl function was found to be necessary to minimize the formation of secondary and higher amines.

Synthesis of derivatives of N-glycyl-β-glycosylamine

1) Dansyl Derivatives

The ammonolysis product (step 3 above) was purified and dansylated according to the method of Gray, *Meth. Enzymol. XXV,* 121 (1971), and the yield compared to that obtained by direct dansylation of lactosylamine (without formation of intermediate N-haloacetylated glycosylamine). The two reaction mixes were run on Silica 60 TLC using 7:1 MeCN/water containing 0.05% diaminobutane. The dansylated products were identified under UV light (366 nm) and these, and the origins (free lactose/N-glycl-lactosylamine) were eluted and counted. The results obtained are shown in Table II, below.

TABLE II

| Product | % of total |
|---|---|
| Dansyl-N-glycyl-lactosylamine | 69.5 |
| N-Glycyl-lactosylamine | 30.5 |
| N-Dansyl-lactosylamine | 10.1 |
| Free lactose | 89.9 |

2. Fluorescein Derivatives

Figure 7:
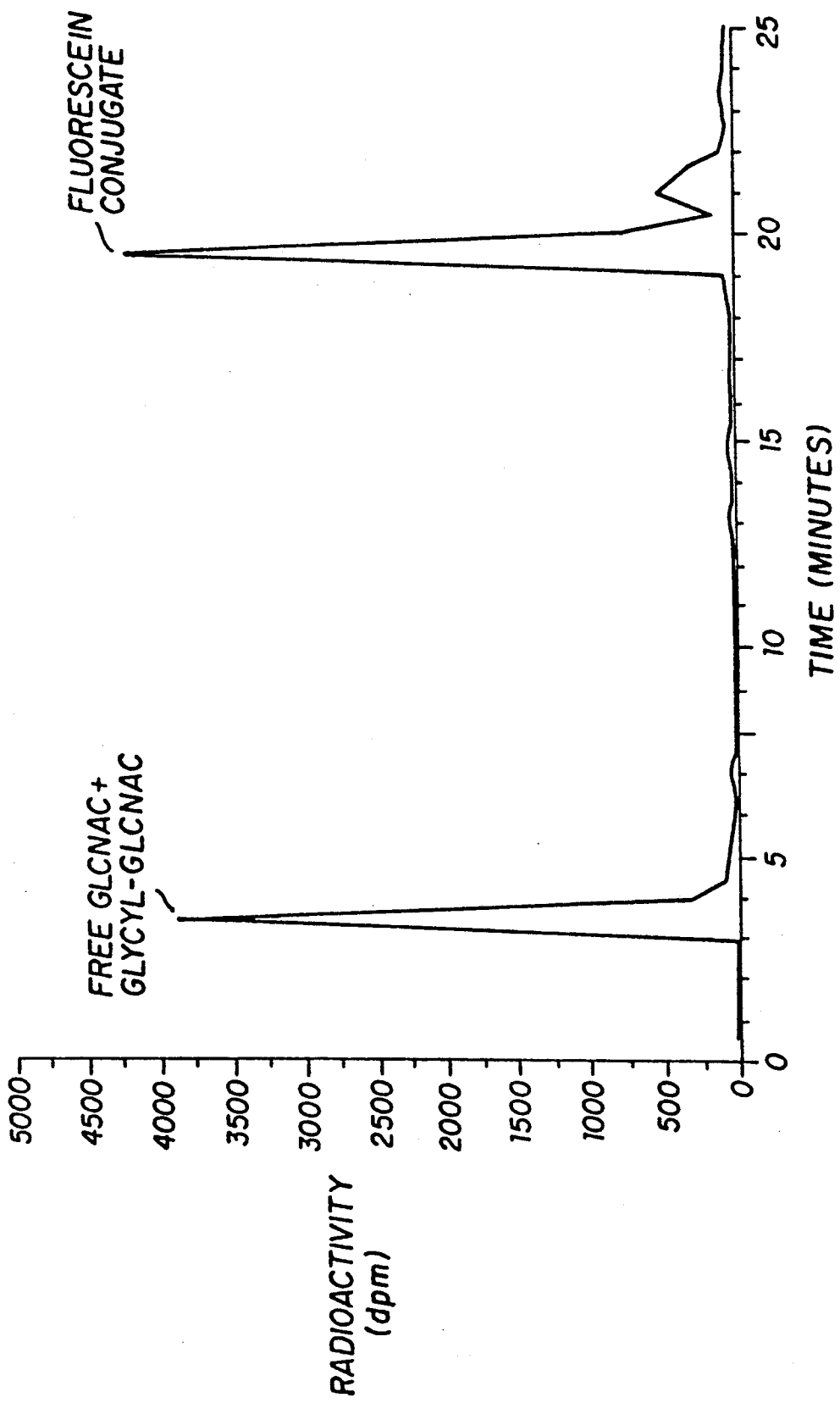
FIG. 7 is a graphical representation which shows the reverse phase HPLC elution profile of a fluorescein derivative of the N-glycyl-glycosylamine derivative of N-acetylglucosamine in another embodiment of the invention.

The N-glycyl-β-glycosylamine derivative of N-acetylglucosamine was dissolved in 100 μl of 0.1M sodium bicarbonate. To this was added 100 μl of DMF containing a 10-fold excess of 5(-6)-carboxyfluorescein-N-hydroxy-succinimidoester (Molecular Probes Inc., Eugene, Oreg.). The reaction was allowed to proceed for 6 hrs at room temperature. The mixture was then dried, redissolved in water, acidified using glacial acetic acid and finally ether extracted to remove free fluorescein. The aqueous phase was then applied to reverse phase HPLC on a Spherisorb S50DS2 SP column (8.0×300 mm), using UV (258 nm) and fluorescence detection (exit. 336 nm-emisc. 536 nm). 50 μl aliquots of the fractions obtained were counted. A typical profile is shown in FIG. 7. Fractions containing free sugar and the fluorescein conjugate were then pooled, dried and counted to obtain the overall yield based on starting sugar shown in Table III below. Similar results were obtained with the derivatives of 5(-6)-carboxytetramethyl-rhodamine -N-hydroxysuccinimidoester (data not shown).

TABLE III

| Product | $^3$H dpm | % of total |
|---|---|---|
| Free GlcNAc | 3.19 E5 | 90.3 |
| Fluorescein-GlcNAc (direct) | 3.43 E4 | 9.7 |
| Free GlcNAc + GlycylGlcNAc | 1.24 E5 | 47.3 |
| Fluorescein-GlycylGlcNAc | 1.38 E5 | 52.6 |

The foregoing data indicate that haloacetylated-glycosylamines are an effective intermediate in the synthesis of β-N-linked saccharide conjugates. Since each of the steps proceeds practically to completion, derivatives in yields approaching 70–80% of total starting compound can be produced.

GENERAL METHOD FOR OLIGOSACCHARIDE DERIVATIZATION

Oligosaccharides
Dissolve in sat. NH$_4$HCO$_3$
Incubate at 30° C. 4 days

↓

Lyophilize with repeated addition of water

↓

N-haloacetylation ⟶ Direct derivatization

↓

Add sat. (NH$_4$)$_2$CO$_3$
Incubate o/n 50° C.

↓

Remove residual glycine, salts

↓

Derivatization of N-glycyl-glycosylamines

See the following reaction scheme for an additional example of the usefulness of these derivatives. It again should be pointed out that the structure of these derivatives includes the amide bond and methylene group found in the biological linkage between N-linked carbohydrates and asparagine in glycoproteins. The reactivity of haloacetylated glycosylamines and glycyl-glycosylamines with, e.g., thioglycolic acid and succinic anhydride, respectively, allow for the incorporation of a terminal carboxy group. This can be used to couple the oligosaccharide to glycopeptides or peptides or proteins by conventional EDC/NHS chemistry [1-ethyl-3-(3-dimethylaminopropyl)-carbodiimide/N-hydroxysuccinimide coupling reactions].

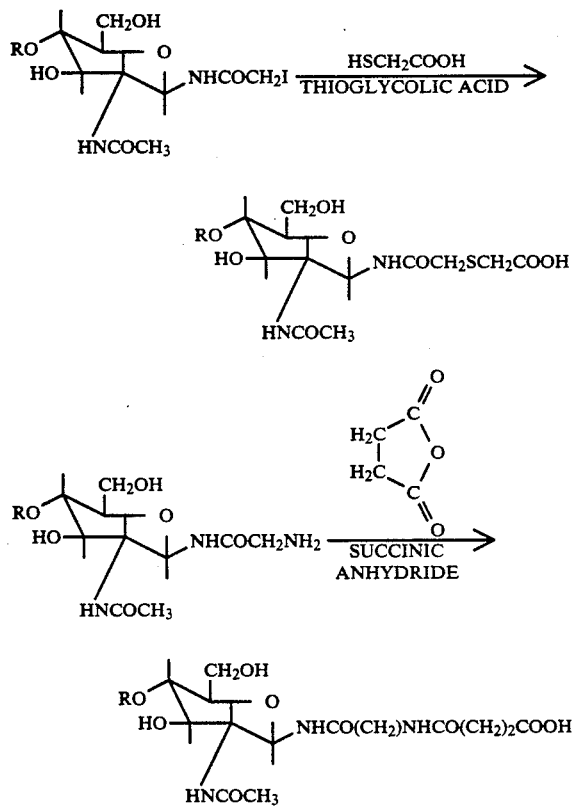

Examples 4 to 9 further illustrate the unique use of the haloacetylated glycosamine intermediate for the synthesis of a variety of N-glycyl-β-glycosylamines or N-linked glycoconjugates embodied in the general Formula III, hereinbefore.

EXAMPLE 4

Method for the Synthesis of Fluorescent-labelled Oligosaccharides

Introduction

Fluorescent-labelled probes have found wide application in cell biology. For example, fluorescent-labelled monoclonal antibodies are routinely used in medical research. FACS-analysis (Fluorescent Activated Cell Sorting) or fluorescent microscopy are widely used methods for their detection.

Figure 8A:
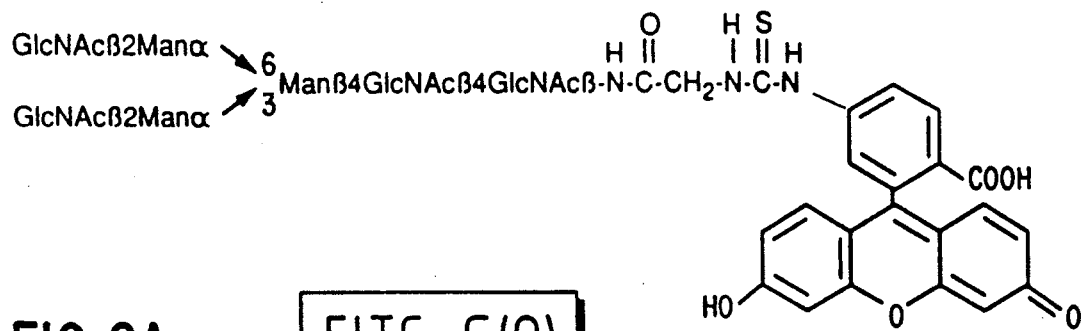
FIG. 8A illustrates a fluorescent-labelled oligosaccharide: structure of (FITC-G(O)) fluorescein derivative of the 1-N-glycyl-β-glycosylamine of GlcNAcβ2-Manα6(GlcNAcβ2Manα3) Manβ4GlcNAcβ4GlcNAcβ4GlcNAc.

It has recently become apparent that cell surfaces contain a variety of cell-surface carbohydrate binding proteins which are important in cell-adhesion events (e.g., Selectins). Fluorescent-derivatives of carbohydrates would therefore have a wide application in the detection of these receptors using either FACS-analysis or fluorescent microscopy. The development of an oligosaccharide fluorescent probe requires a chemical approach which retains the ring structure of the reducing terminal monosaccharide residue, the anomericity of this residue and an appropriate linker to the probe which mimics the biological attachment. This example illustrates the synthesis of the 1-N-glycyl-β-derivative of an oligosaccharide, and reaction of this compound with fluorescein isothiocyanate (FITC) to produce a fluorescent-derivative (FIG. 8A). This synthesis is of general applicability such that any carbohydrate that contains a reducing terminal oligosaccharide may be converted into fluorescent derivatives.

Methods

Synthesis of Fluorescent-Carbohydrate Conjugates

1. Preparation of Glycosylamine. Formation of the glycosylamine of G(O)=GlcNAc β2 Man α3 (GlcNAc β2 Man α6) Man β4 GlcNAc β4 GlcNAc was performed as follows: One mg of oligosaccharide was rotoevaporated to dryness and resuspended in 200 μl of saturated ammonium bicarbonate (1M) made up with sterile water. Solid ammonium bicarbonate was then added to maintain saturation of the solution during the incubation period. The tubes were sealed with Parafilm which was then punctured using a needle (to allow the escape of the ammonia and carbon dioxide evolved by decomposition of the salt). After incubation at 30° C. for 3-4 days, the G(O) glycosylamine preparation was desalted by direct lyophilization of the reaction mixture in 1 ml of distilled water.

2. Preparation of N-Glycvl Derivative (a) N-chloroacetvlation of Glycosylamines. G(O) glycosylamine was converted to the 1-N-glycyl-β-derivative via the N-chloroacetamido derivative using a combination of N-chloroacetylation and ammonolysis. G(O) glycosylamine was dissolved in 100 μl of 1M sodium bicarbonate and cooled on ice. To this was added 5-fold molar excess of solid chloroacetic anhydride, and the reaction mixture was allowed to warm to room temperature. The pH was maintained at or above 7.0 by adding sodium bicarbonate when necessary. Progress of the reaction was monitored by thin layer chromatography (TLC) using acetonitrile/water 7:4 (v/v) and 0.05% diaminobutane as solvent. A total of 3 hr was required to complete the reaction. Following chloroacetylation, the mixture was desalted by passage over a column containing Dowex AG50-X12(H+) cation exchange resins layered on top of AG3-X4A(OH−)anion exchange resins. The eluant was collected and evaporated to dryness, resuspended in 200 μl of water prior to analysis by ¹H-NMR and TLC.

(b) Ammonolysis of N-chloracetylated glycosylamine. The chloroacetylated glycosylamine was dissolved in 500 μl of saturated ammonium bicarbonate, sealed in a glass tube to prevent loss of ammonia by evaporation and incubated at 50° C. overnight. The ammonium bicarbonate was then removed by direct lyophilization in 1 ml distilled water.

Figure 8B:
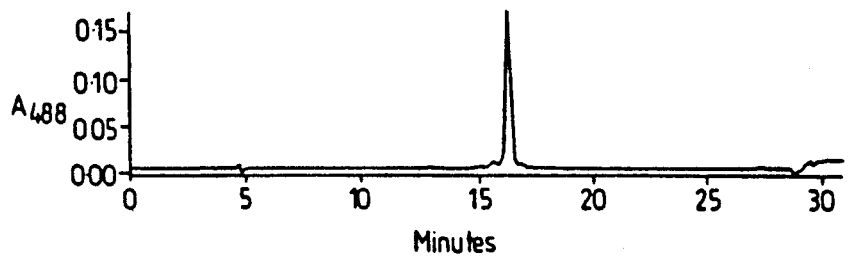
FIG. 8B illustrates a fluorescent-labelled oligosaccharide: HPLC chromatogram with fluorescent detection showing the mobility and purity of the FITC-G(O).
Figure 8C:
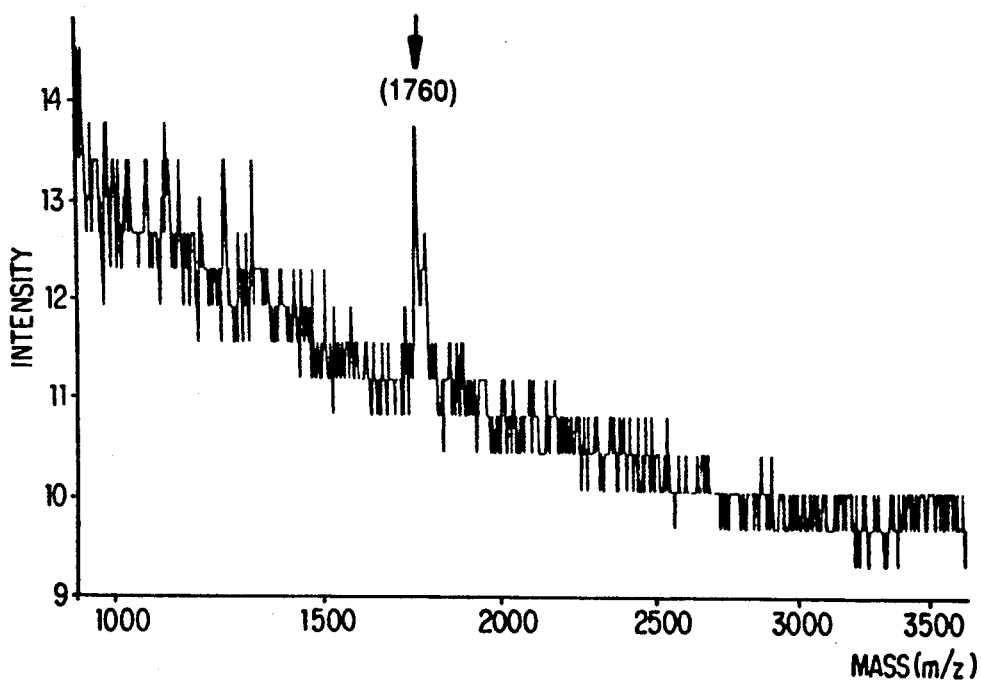
FIG. 8C illustrates a fluorescent-labelled oligosaccharide: Laser desorption mass-spectrometric analysis confirming the molecular weight of the expected compound at 1,760 m/z.

3. Conjugation to Fluorescein Isothiocyanate. The 1-N-glycyl-β-derivative of G(O) oligosaccharide was dissolved in 100 μl of 0.1M NaHCO₃, pH 10, and was mixed with FITC (10-fold molar excess) dissolved in MeOH. The reaction was stirred overnight at room temperature. The mixture was analysed by TLC using acetonitrile/water 7:4 (v/v) and 0.05% diaminobutane as solvent. $R_f$ values for FITC, FITC-G(O), and glycyl G(O) were 0.76, 0.57, and 0.03, respectively. The band representing the FITC-G(O) was wetted with a small quantity of water and scraped off into a microcentrifuge tube. Silica was washed and centrifuged with water, for 4-5 times. Supernatant was dried and resuspended in 100 μl water. It was further purified by reverse phase HPLC on a S50DS2 column (8×250 mm) using a 0-50% gradient of water and acetonitrile containing 0.1% trifluoroacetic acid for 30 mins (FIG. 8B). The mass of purified FITC-G(O) was determined by laser desorption mass spectrometry using a LASERMAT machine (FinneganMat, Hemel Hempstead, Hertfordshire, U.K.) (FIG. 8C).

EXAMPLE 5

Method for the Derivatization of Plastic Surfaces with Carbohydrates

Introduction

Adsorption of proteins to plastic surfaces such as performed in enzyme linked immunosorbent assay (ELISA) based assays has revolutionized diagnostic medicine. To date no adequate method exists for the attachment of carbohydrate ligands to plastic surfaces in a manner which retains the integrity of the terminal reducing monosaccharide and its linkage to protein.

Many carbohydrate binding proteins recognize the reducing terminal monosaccharide along with other more peripheral carbohydrate epitopes (i.e. *Lens culinaris* lectin). Maintaining the integrity of these residues is important in the binding of this lectin. The ability to immobilize carbohydrate on plastic surfaces is an important diagnostic aid in detecting both cell-surface as well as circulating carbohydrate binding patents.

Figure 9:
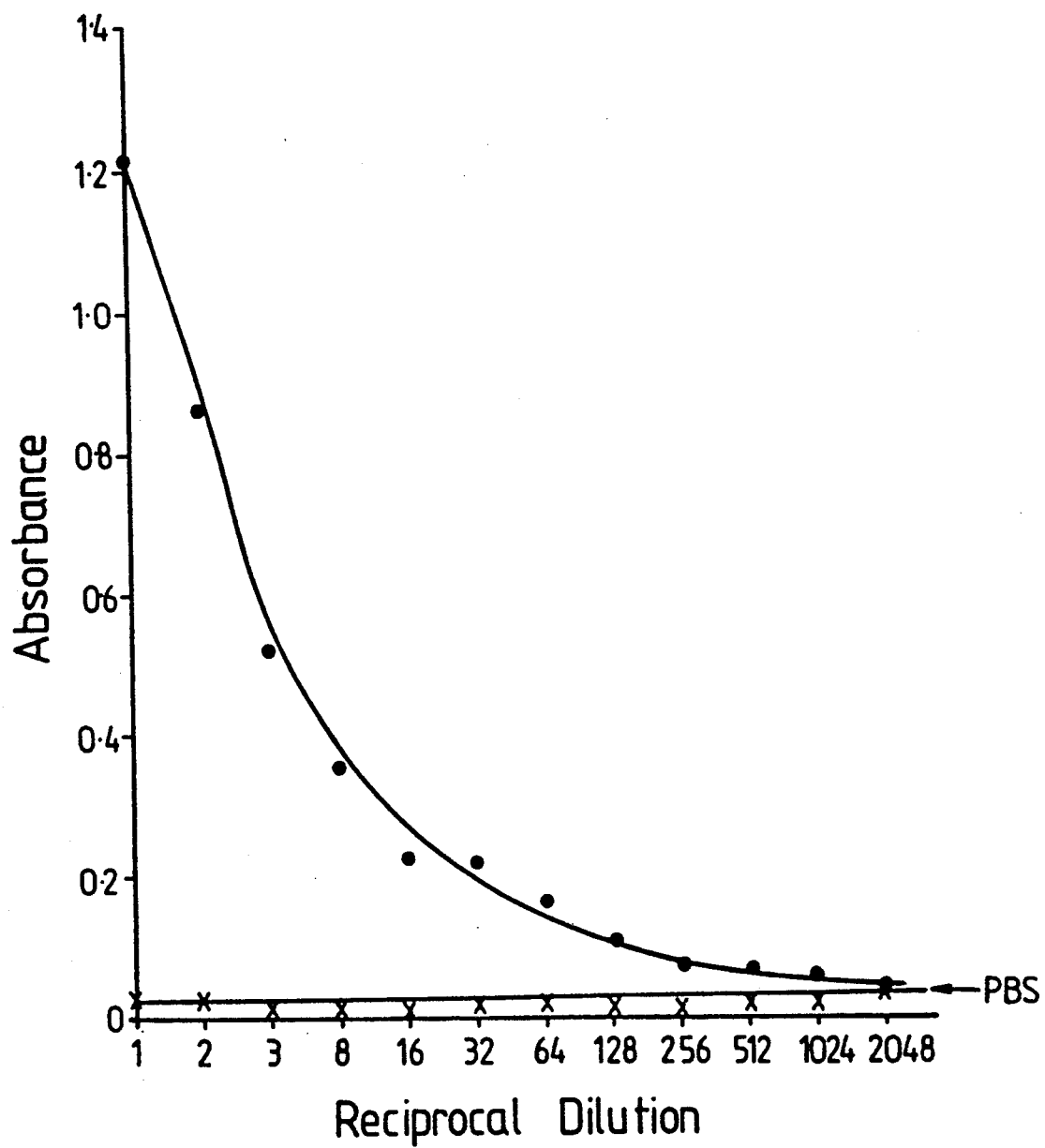
FIG. 9 is a graphical representation which shows the binding of IgM anti-GlcNAc antibody (GN7) to a Falcon Premaria Petri dish derivatized with N'N'-diacetylchitobiose. X, PBS control; solid dots, different dilutions of the anti GN7 antibody.

This example illustrates the synthesis of the 1-N-glycyl-β-derivative of an oligosaccharide, its reaction with thiophosgene to give the thiocyanate derivative and the coupling of the latter to surface modified plastic Falcon Primaria tissue culture plates. The utility of this method is demonstrated by the binding of an anti-carbohydrate monoclonal antibody to the plate (FIG. 9).

Methods

Immobilization of Carbohydrates onto Falcon Elisa Plates.

1. Preparation of Glycosylamine. Formation of the glycosylamine of N,N'-diacetylchitobiose was performed as follows: Five mg of the sugar sample was roto-evaporated to dryness and resuspended in 200 μl of saturated ammonium bicarbonate (1M) made up with sterile water. Solid ammonium bicarbonate was then added to maintain saturation of the solution during the incubation period. The tubes were sealed with Parafilm which was then punctured using a needle (to allow the escape of the ammonia and carbon dioxide evolved by decomposition of the salt). After incubation at 30 C for 3-4 days, the glycosylamine preparation was desalted by direct lyophilization of the reaction mixture in 1 ml of distilled water.

2. Preparation of N-Glycyl Derivative (a) N-chloroacetvlation of Glycosylamine. The glycosylamine was converted to the 1-N-glycyl-β-derivative via the N-chloroacetamido derivative using a combination of N-chloroacetylation and ammonolysis. The glycosylamine was dissolved in 100 μl of 1M sodium bicarbonate and cooled on ice. To this was added 5-fold molar excess of solid chloroacetic anhydride, and the reaction mixture was allowed to warm to room temperature. The pH was maintained at or above 7.0 by adding sodium bicarbonate as necessary. Progress of the reaction was monitored by thin layer chromatography (TLC) using acetonitrile/water 7:4 (v/v) and 0.05% diaminobutane as solvent. A total of 3 hr was required to complete the reaction. Following chloroacetylation, the mixture was desalted by passage over a column containing Dowex AG50-X12 (H+) cation exchange resins layered on top of AG3-X4A (OH−) anion exchange resins. The eluant was collected and evaporated to dryness, resuspended in 200 μl of water prior to analysis by $^1$H-NMR and TLC.

(b) Ammonolysis of N-chloroacetylated Glycosylamines. The chloroacetylated mixture was dissolved in 500 μl of saturated ammonium bicarbonate, sealed in a glass tube to prevent loss of ammonia by evaporation and incubated at 50° C. overnight. The ammonium bicarbonate was then removed by direct lyophilization in 1 ml distilled water.

3. Preparation of N-glycyl Isothiocyanate Derivative. The 1-N-glycyl-β-derivative of N,N'-diacetylchiobiose was dissolved in 1 ml of 0.1M NaHCO$_3$, pH 8.5, and layered over 1.25 ml of chloroform containing thiophosgene (2.5-fold molar excess). The reaction mixture was stirred for at least an hour at room temperature in a ventillated fume hood. The reaction mixture was extracted four times with 1 ml of chloroform. The top aqueous layer after the final spin of the mixtures in an Eppendorf centrifuge was carefully removed.

4. Conjugation to Amino-derivatized Falcon ELISA Plate. The 1-N-glycyl-β-isothiocyanate derivative N,N'-diacetylchiotobiose (12 μmole/ml) was conjugated to an amino-derivatized ELISA plate (Falcon). One hundred μl of the aqueous layer was serially diluted two fold in 0.3M NaCl in 0.1M NaHCO$_3$, pH 10, and 50 μl of each dilution was added to the plate. Following overnight incubation at room temperature, the plate was rinsed thoroughly with phosphate buffered saline (PBS) to remove unbound sugar. The plate was quenched with 4% bovine serum albumin (BSA) in PBS prior to the binding of an anti-GlcNAc antibody. Detection of the primary antibody (IgM subclass) was performed by incubating the plate with an anti-μ antibody covalently conjugated to horse radish peroxidase (HRP). The plate was developed using 50 μl of the substrate 2,2'-Azinobis(3-ethylbenzthiazolinesulfonic acid) (ABTS) (12.5 mg/ml). Absorbance at 499 nm and 620 nm was read by a plate reader (FIG. 9). For negative controls, the plate was incubated with PBS alone or in the presence of a competitive inhibitor, GlcNAc (60 mM).

EXAMPLE 6

Method for the Synthesis of Lipoglycan Immunomodulators

Introduction

Antigen presentation is crucial in the immune response. Exogeneously administered peptides usually fail to initiate a primary response during immunization. Lipopeptide vaccines in contrast are able to prime lymphocytes for an immune response following antigen challenge. Lipopeptide vaccines consist of peptides attached to the carrier P$_3$CSS (tripalmitoyl-S-glycerylcysteinyl-seryl-serine) or P₃C (tripalmitoyl-S-glyceryl-cysteine).

The P₃CSS or P₃C is believed to mediate attachment to the cell membrane, internalization into the cytoplasm and activate macrophages to secret cytokines. While immune response against peptides have been extensively studied, the mechanism of the immune response against carbohydrate antigens is unknown. Indeed an immune response against carbohydrates may be crucial in protective immunization against a whole host of infectious agents including viruses, bacteria, micobacteria and parasites.

Further, the inappropriate anti-carbohydrate immune response against carbohydrate may be important in a number of autoimmune diseases. Modulating that response may be curcial in therapy.

This example illustrates the synthesis of a P₃C conjugate of a carbohydrate via the use of or the 1-N-glycyl-β-carbohydrate derivatives. This chemistry is important in the development of novel agents for both the prevention and therapy of a number of diseases.

Methods

Lipoglycan Synthesis.

1. Preparation of Glycosylamine. Formation of the glycosylamine of N,N'-diacetylchitobiose was performed as follows: Six mg of the sugar was roto-evaporated to dryness and resuspended in 200 μl of saturated ammonium bicarbonate (1M) made up with sterile water. Solid ammonium bicarbonate was then added to maintain saturation of the solution during the incubation period. The tubes were sealed with Parafilm which was then punctured using a needle (to allow the escape of the ammonia and carbon dioxide evolved by decomposition of the salt). After incubation at 30° C. for 3-4 days, the glycosylamine preparation was desalted by direct lyophilization of the reaction mixture in 1 ml of distilled water.

2. Preparation of N-Glycyl Derivative.

(a) N-chloroacetylation of Glycosylamine. The glycosylamine of N,N'-diacetylchitobiose was converted to the 1-N-glycyl-β-derivative via the N-chloroacetamido derivative using a combination of N-chloroacetylation and ammonolysis. The glycosylamine was dissolved in 100 μl of 1M sodium bicarbonate and cooled on ice. To this was added 5-fold molar excess of solid chloroacetic anhydride, and the reaction mixture was allowed to warm to room temperature. The pH was maintained at or above 7.0 by adding sodium bicarbonate as necessary. Progress of the reaction was monitored by thin layer chromatography (TLC) using acetonitrile/water 7:4 (v/v) and 0.05% diaminobutane as solvent. A total of 3 hr was required to complete the reaction. Following chloroacetylation, the mixture was desalted by passage over a column containing Dowex AG50-X12 (H+) cation exchange resins layered on top of AG3-X4A (OH−) anion exchange resins. The eluant was collected and evaporated to dryness, resuspended in 200 μl of water prior to analysis by ¹H-NMR and TLC.

(b) Ammonolysis of N-chloroacetylated Glycosylamine. The chloroacetylated mixture was dissolved in 500 μl of saturated ammonium bicarbonate, sealed in a glass tube to prevent loss of ammonia by evaporation and incubated at 50° C. overnight. The ammonium bicarbonate was then removed by direct lyophilization in 1 ml distilled water.

3. Conjugation to P₃C.

A mixture containing 7 μmole of the N-glycyl derivative of N,N'-diacetylchitobiose in 68 μl DMSO and 40 μl DMF, 2 μmole of P₃C in 40 ml DMF/dichloromethane (1:1), and 4 μmole of HBTU/HOBT in 120 μl DMF was stirred for two days at room temperature.

The mixture was stored overnight at −20° C. after the coupling reaction. One ml chloroform/methanol (1:1) was then added to recrystallize P₃C. The mixture was left overnight at −20° C. prior to spinning the mixture in an Eppendorf centrifuge at maximum speed for 10 mins. The supernatant was carefully removed. A small white precipitate was resuspended in 40 μl of t-butanol/water (4:1) and analyzed along with unconjugated P₃C by TLC.

HOBT = 1-hydroxybenzotriazole
HBTU = 2-(1H-benzotriazol-1-yl)-1,1,3,3-tetramethyluronium-hexafluorophosphate.

EXAMPLE 7

Method for Glycopeptide Synthesis

Synthesis of a Atriopeptin Neoglycohormone

Introduction

Synthetic peptides are of enormous importance in both medical research, diagnosis and therapy. Many synthetic small bioactive hormones have potential pharmacologic uses if sufficient serum half-life can be attained. Clearance by specific cellular receptors or non-specific clearance via the bile or kidney reduces the half-life of many of these molecules to minutes. Synthesis of a glycosylated form of a peptide would be desirable as it will have increased stability and half-life in serum.

Synthetic peptide vaccines can also have limited efficacy if the T-cell recognition peptide is glycosylated. For example, T-cells from rabies-immune mice can be stimulated with cyanogen bromide fragments of the rabies virus glycoprotein. Synthetic analogs of two fragments CR2 and CR3 (which are both glycosylated in virus derived material) do not stimulate the T-cells. This indicates that it is the glycopeptide and not the peptide which is recognized. Synthesis of a glycopeptide would in this case be useful as a synthetic vaccine. Glycopeptides containing large oligosaccharides of biological origin have not been chemically synthesized heretofore.

This example illustrates the synthesis of glycopeptides using direct coupling of unprotected glycosylamine derivatives of oligosaccharides. The example further demonstrates the utility by the synthesis of two different glycosylated forms of the bioactive hormones known as atriopeptins. Atriopeptins I, II and III as described, e.g., in U.S. Pat. No. 4,496,544, are typical of the useful peptides.

Methods

Synthesis of Glycopeptides

1. Preparation of Glycosylamines. Formation of the glycosylamines of N,N'-diacetylchitobiose and Man α3 (Man α6) (Xyl β2) Man β4 GlcNAc β4 (Fuc α6) GlcNAc and Galβ4GlcNAcβ2Manα6(Galβ4GlcNAc-Manα3)Manβ4-GlcNAcβ4GlcNAc and were performed as follows: Five mg of N,N'-diacetylchitobiose, one mg of Man α3 (Man α6) (Xyl β2) Man β4 GlcNAc β4 (Fuc α6) GlcNAc and 1 mg of Galβ4GlcNAcβ2-Manα6(Galβ4GlcNAcManα3)Manβ4-GlcNAcβ4GlcNAc were roto-evaporated to dryness and resuspended in 200 μl of saturated ammonium bicarbonate (1M) made up with sterile water. Solid ammonium bicarbonate was then added to maintain saturation of the solution during the incubation period. The tubes were sealed with Parafilm which was then punctured using a needle (to allow the escape of the ammonia and carbon dioxide evolved by decomposition of the salt). After incubation at 30° C. for 3–4 days, the glycosylamine preparations were desalted by direct lyophilization of the reaction mixtures in 1 ml of distilled water. The glycosylamine samples were analyzed by TLC and $^1$H-NMR.

Figure 11A:
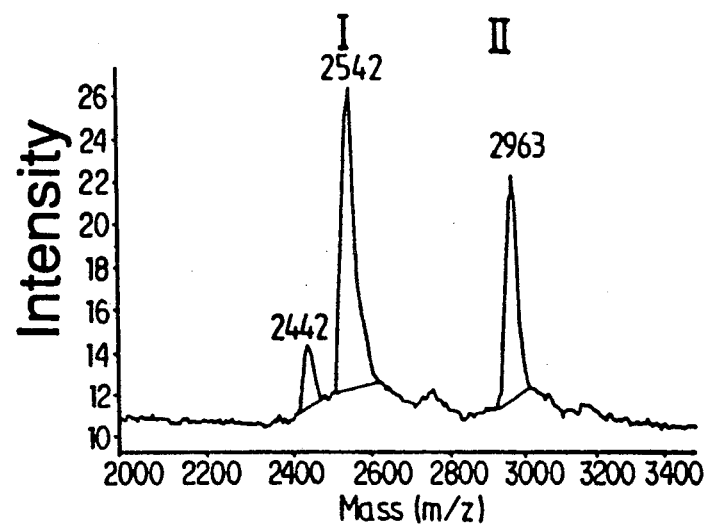
FIG. 11A shows the laser desorption mass-spectrometry showing the molecular mass of atriopeptin A following derivatization with N'N-diacetylchitobiose. Analogue A: starting material m/z 2,542; plus sugar 2,963 mz.
Figure 11B:
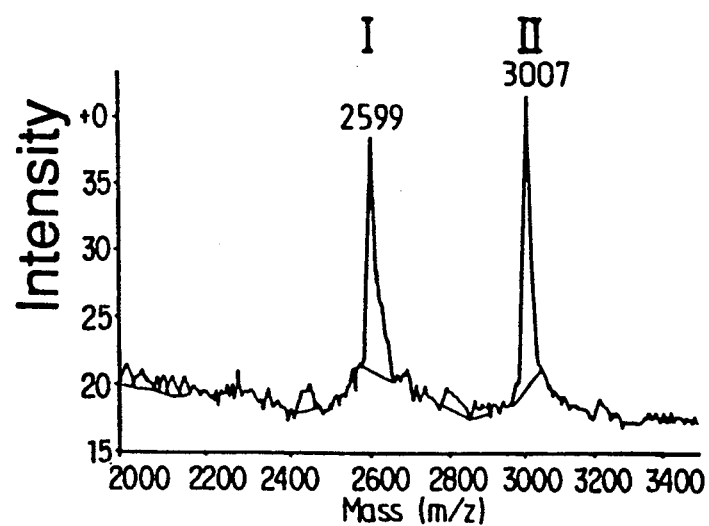
FIG. 11B shows the laser desorption mass spectrometry showing the molecular mass of atriopeptin D following derivatization with N'N'-diacetylchitobiose. Analogue D: starting material m/z 2,599; plus sugar 3,007 m/z.
Figure 12A:
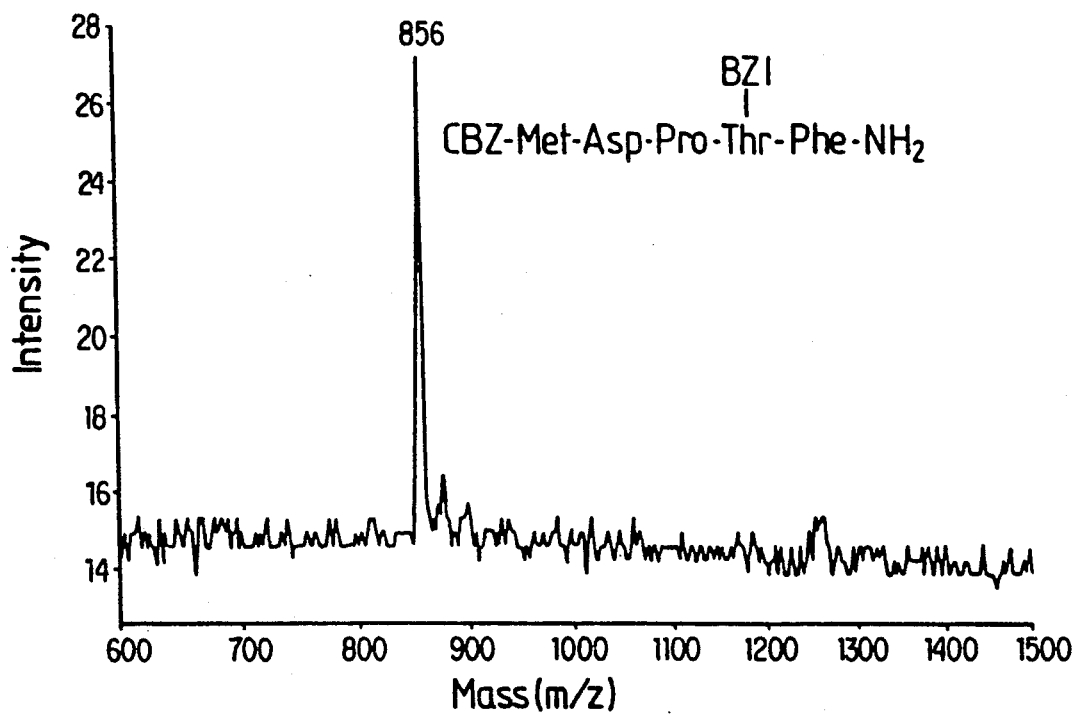
FIG. 12A shows the laser desorption mass-spectrometry showing the molecular mass of the indicted peptide before derivatization.
Figure 12B:
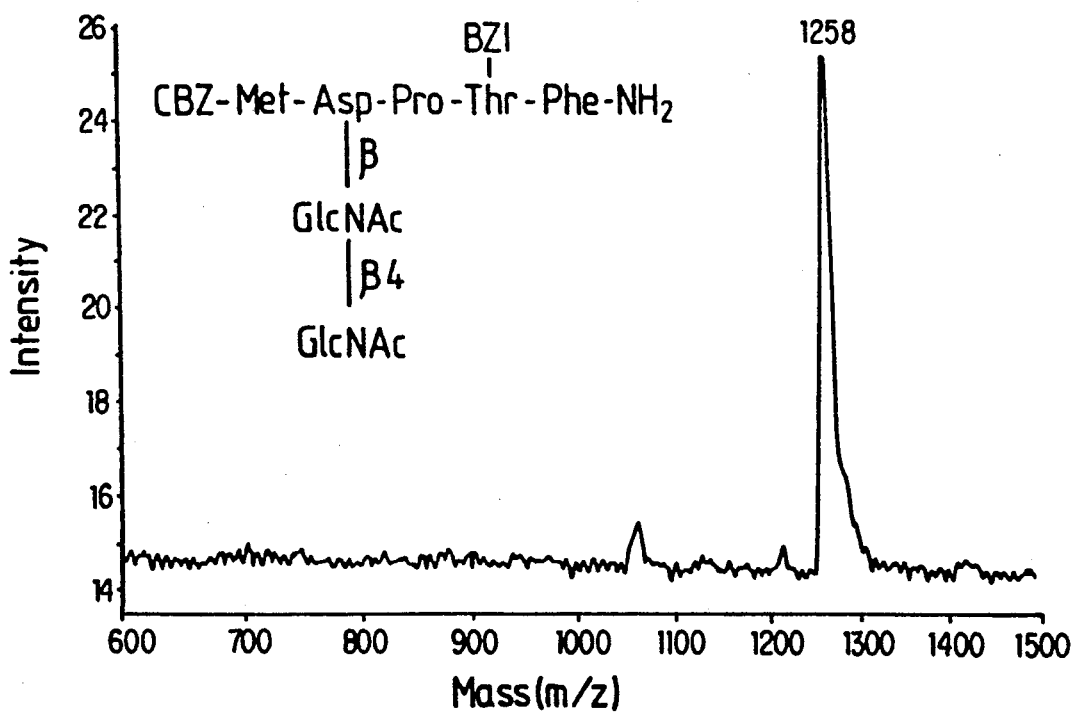
FIG. 12B shows the laser desorption mass-spectrometry showing the molecular mass of the indicted peptide after derivatization.

2. Coupling of Glycosylamines to Synthetic Peptides. The glycosylamines of N,N'-diacetylchitobiose, Man α3 (Man α6) (Xyl β2) Man β4 GlcNAc β4 (Fuc α6) GlcNAc and Galβ4GlcNAcβ2Manα6(Galβ4GlcNAc-Manα3)Manβ4-GlcNAcβ4GlcNAc were coupled to synthetic peptides CBZ-Met-Asp-Pro-Thr(Bzl)-Phe-NH$_2$, CBZ-Met-Asp-Pro-Ser(Bzl)-Phe-NH$_2$ and FMOC-Ala-Glu-Ala-Thr-Phe-NH$_2$, respectively, using the following procedure: Five μmole of respective peptide (3.5 mg) in 50 μL DMF was added to 10 μmole of N,N'-diacetylchitobiose glycosylamine (3.7 mg) or 1 μmole of Man α3 (Man α6) Xyl β2) Man β4 GlcNAc β4 (Fuc α6) GlcNAc glycosylamine in 85 μL DMSO and 50 μL DMF. For 0.6 μmole of Galβ4GlcNAcβ2-Manα6(Galβ4GlcNAcManα3)Manβ4-GlcNAcβ4GlcNAc, only 2 μmoles of FMOC-Ala-Glu-Ala-Thr-Phe-NH$_2$ peptide was used for coupling. A coupling reagent HBTU (15 μmole in 100 μL DMF and a catalyst HOBT (5 μmole in 50 μL DMF) were added to the mixture of glycosylamines and peptides. The reaction mixtures were stirred at room temperature in a Pierce glass vial and analyzed for glycopeptide synthesis by HPLC C4 analytical column (elution condition: 5–100% acetonitrile in 20 mins). Glycopeptide synthesis occurred in 4 hrs for N,N'-diaoetylchitobiose glycosylamine compared to 4–5 days for Man α3 (Man α6) (Xyl β2) Man β4 GlcNAc β4 (Fuc α6) GlcNAc glycosylamine and 1 day for Galβ4GlcNAcβ2Manα6(Galβ4GlcNAc-Manα3)Manβ4-GlcNAcβ4GlcNAc. The products were analyzed by the Picotag method for the presence of sugar and amino acid composition and for mass by laser desorption mass spectrometry using a Lasermat machine (FIGS. 11 and 12).

Attachment of Sugar to Atriopeptin Analogs

1. Preparation of Glycosylamine. Formation of the glycosylamine of N,N'-diacetylchitobiose was perforemed as follows: Five mg of N,N'-diacetylchitobiose was roto-evaporated to dryness and resuspended in 200 μl of saturated ammonium bicarbonate (1M) mae up with sterile water. Solid ammonium bicarbonate was then added to maintain saturation of the solution during the incubation period. The tube was sealed with Parafilm which was then punctured using a needle (to allow the escape of the ammonia and carbon dioxide evolved by decomposition of the salt). After incubation at 30° C. for 3–4 days, the glycosylamine preparation was desalted by direct lyophilization of the reaction mixtures in 1 ml of distilled water. The glycosylamine sample was analyzed by TLC and $^1$H-NMR.

Figure 10:
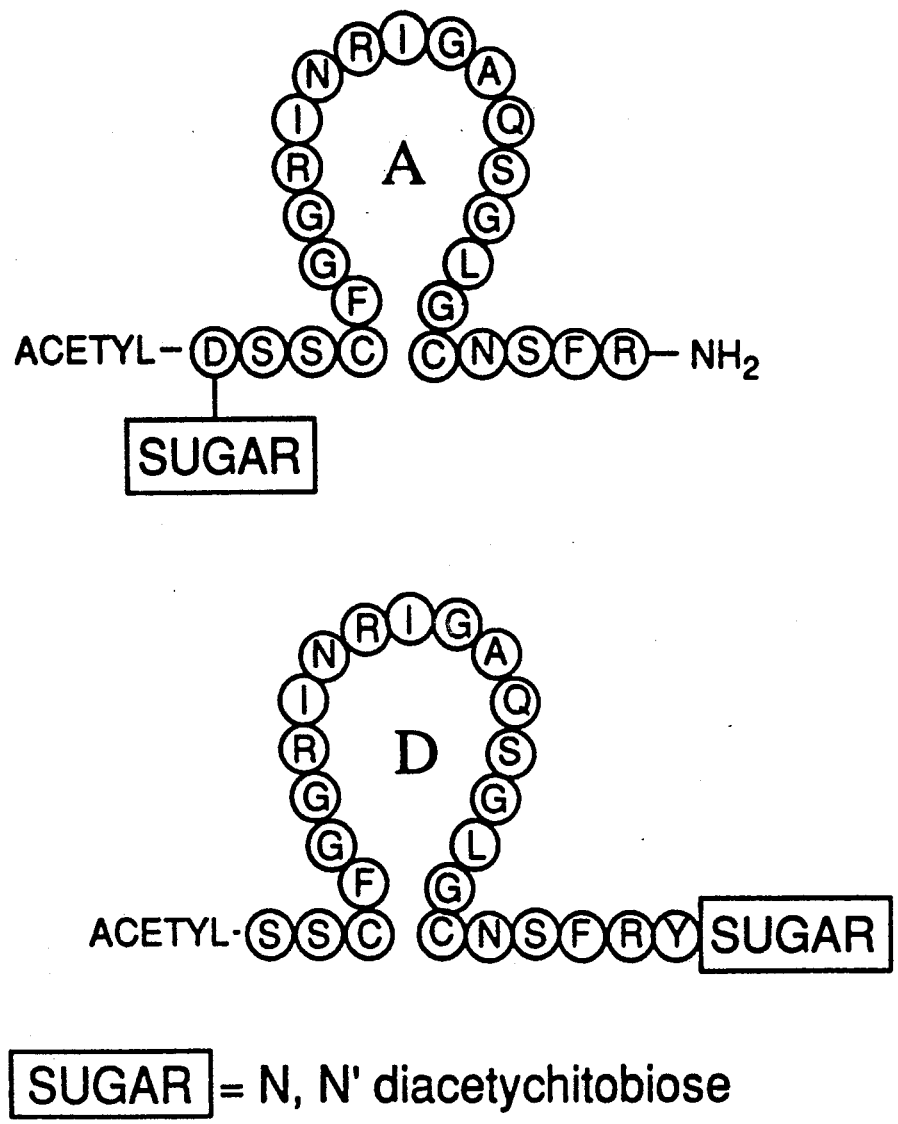
FIG. 10 is a schematic representation of the neoglycopeptide analogues of atriopeptins A and D. The position of the sugar attachment is shown by the boxes.
Figure 13:
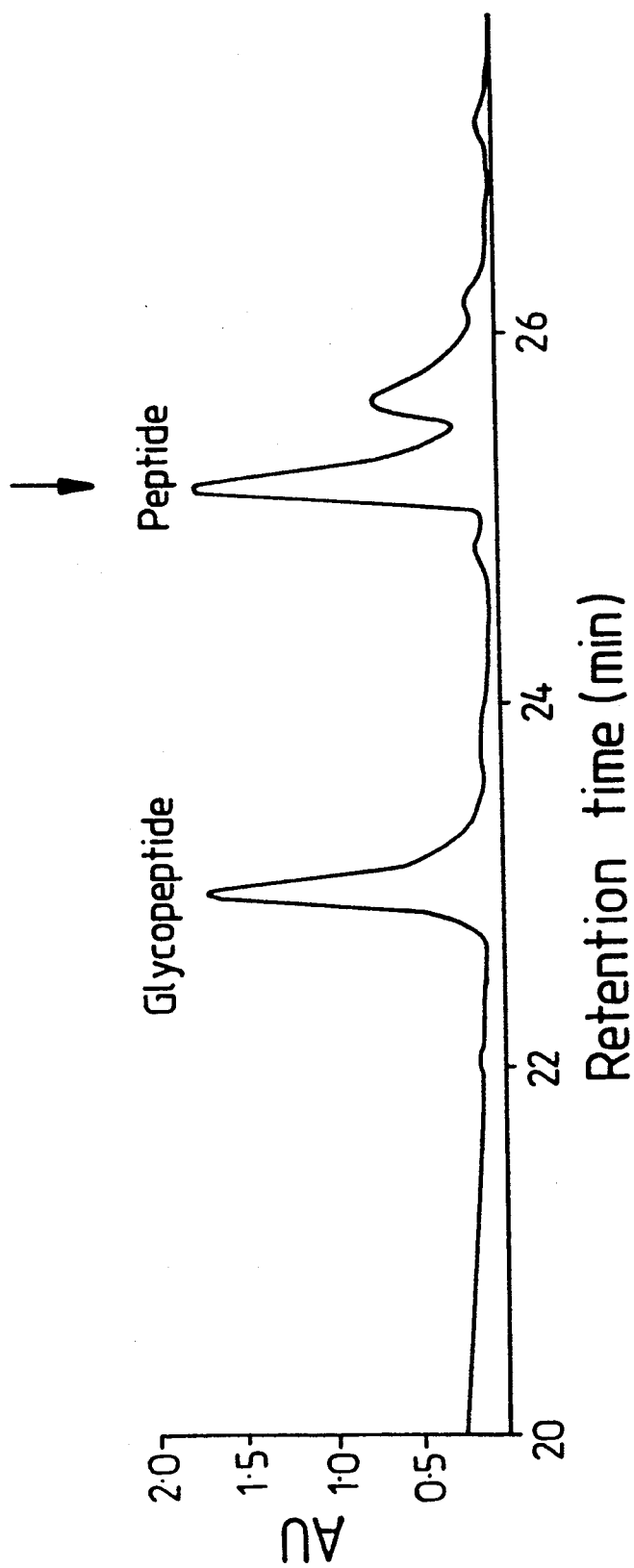
FIG. 13 shows the HPLC chromatogram of the reaction mixture of the $\beta$-glycosylamine of Gal$\beta$4GlcNAc$\beta$2Man$\alpha$6(Gal$\beta$4GlcNAc$\beta$2Man$\alpha$3) Man$\beta$4GlcNAc$\beta$4GlcNAc and FMOC-Ala-Glu-Ala-Thr-Phe-NH$_2$ in the presence of HOBT and HBTU. The arrow indicates the position of the peptide.
Figure 14:
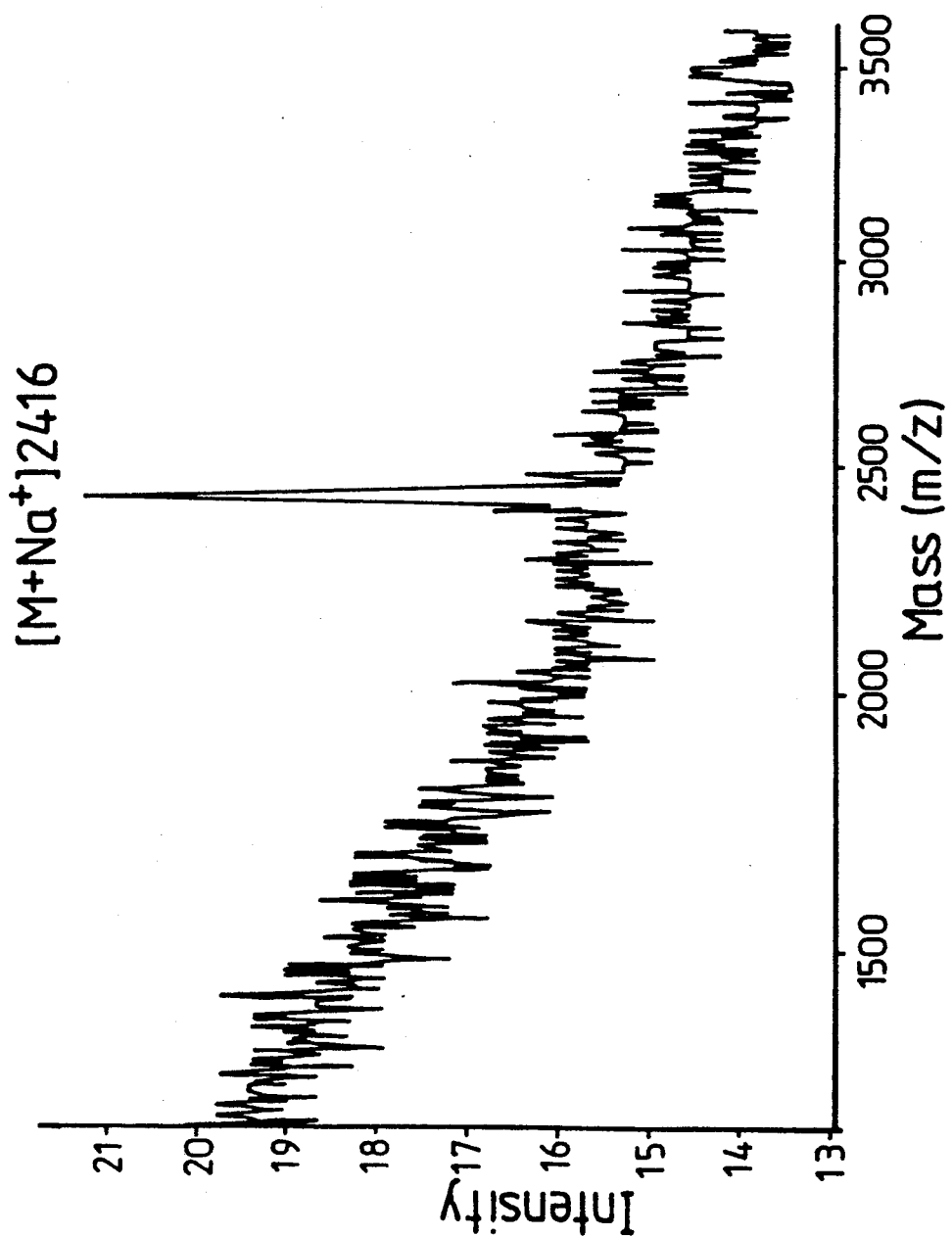
FIG. 14 shows the laser desorption-mass-spectrometry of the glycopeptide formed by the reaction of the $\beta$-glycosylamine of Gal$\beta$4GlcNAc$\beta$2Man$\alpha$6(Gal$\beta$4GlcNAc$\beta$2Man$\alpha$3) Man$\beta$4GlcNAc$\beta$4GlcNAc and FMOC-Ala-Glu-Ala-Thr-Phe-NH$_2$ in the presence of HOBT and HBTU.
Figure 15A:
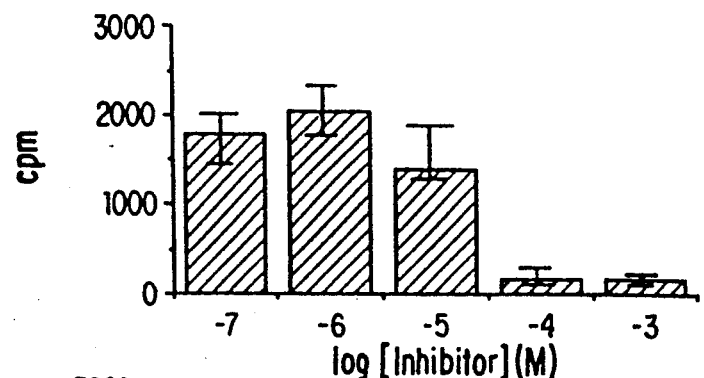
FIG. 15A is a graphical representation which shows the effect of the neoglycoprotein HSA-gentiobiose on lymphocyte proliferation in a mixed lymphocyte reaction (MLR): Various concentration of gentiobiose alone.
Figure 15B:
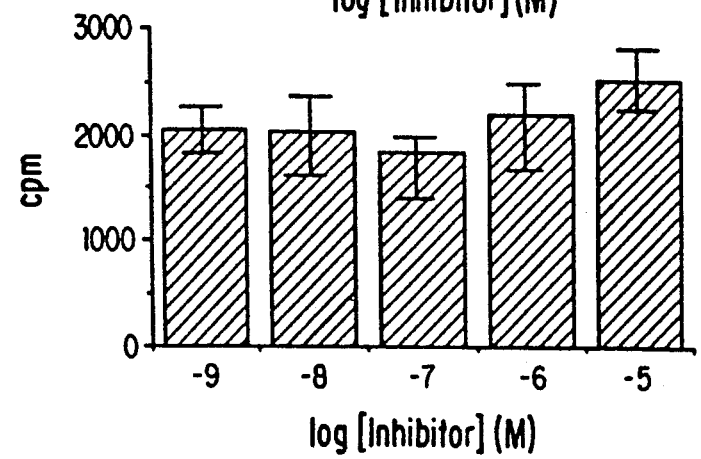
FIG. 15B is a graphical representation which shows the effect of the neoglycoprotein HSA-gentiobiose on lymphocyte proliferation in a mixed lymphocyte reaction (MLR): HSA.
Figure 15C:
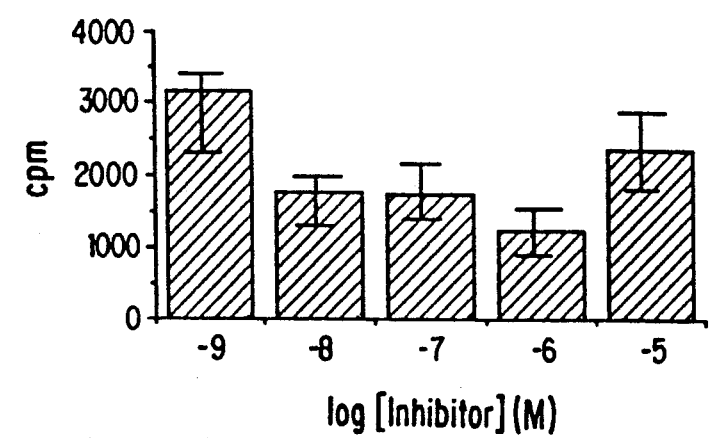
FIG. 15C is a graphical representation which shows the effect of the neoglycoprotein HSA-gentiobiose on lymphocyte proliferation in a mixed lymphocyte reaction (MLR): HSA (gntiobiose)$_5$.
Figure 15D:
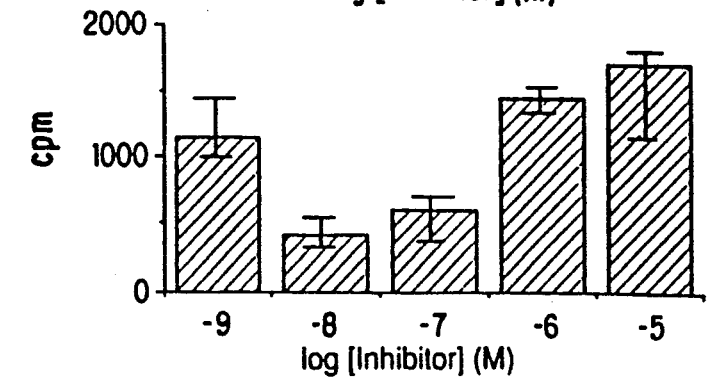
FIG. 15D is a graphical representation which shows the effect of the neoglycoprotein HSA-gentiobiose on lymphocyte proliferation in a mixed lymphocyte reaction(MLR): HSA (gentiobiose)$_{30}$ were added to MLR cultures.

2. Coupling of Glycosylamine to Atriopeptin Analogs. The glycosylamine of N,N'-diacetylchitobiose was coupled to atriopeptin analogs A and D (FIG. 10) using the following procedure: One mg of peptide (0.4 μmole) in 50 μL DMF was added to i μmole of N,N'-diacetylchitobiose glycosylamine in 85 μL DMSO and 50 μL DMF. A coupling reagent HBTU (1.2 μmole in 100 μL DMF) and a catalyst HOBT (0.5 μmole in 50 μL DMF) were added to the mixture of glycosylamine and peptide. The reaction mixtures were stirred at room temperature in a Pierce Glass vial and analyzed for glycopeptide synthesis by HPLC C4 analytical column (elution condition: 5–100% acetonitrile in 20 mins) (FIG. 13). Glycopeptide synthesis occurred in 4 hrs. The products were analyzed by the Picotag method for the presence of sugar and amino acid composition and for mass by laser desorption mass spectrometry using a Lasermat machine (FIG. 14).

EXAMPLE 8

Method for the Synthesis of Neoglycoproteins

Synthesis of an Immunosuppressive Neoglycoprotein

Introduction

Glycoproteins by far constitute the largest class of proteins. Almost all cell-surface and circulating proteins in mammalian, plant, insect tissue, etc., contain attached carbohydrates either through O-linkage to serine or threonine or N-linkage to asparagine. Further, a large number of carbohydrate binding proteins are found either circulating or cell-surface associated. A characteristic of these carbohydrate binding proteins is that they can be cross-linked by the glycoprotein. This arises from the fact that most glycoproteins contain multiple glycosylation sites or contain more than one glycosylated subunit.

The glycosylation of glycoproteins is heterogeneous. Glycoproteins therefore consist of a population of glycoforms (same peptide but different carbohydrates). It is the qualitative and quantitative changes in the relative molar proportion of each glycoform which makes glycosylation cell-type specific. Heretofore there was no way to experimentally produce a glycoprotein of uniform glycosylation nor to separate a glycoform population into separate glycoforms. It is therefore desirable to have a method for producing glycoforms of uniform carbohydrate structure and having multiple carbohydrate chains per protein.

This example illustrates the synthesis of the 1-N-glycosyl-β-derivative of carbohydrates, the reaction of these compounds with thiophosgene to give the isothiocyanate and the reaction of these intermediates with non-glycosylated protein carriers. One of these, gentiobiose—HSA, is capable of inhibiting the mixed lymphocyte reaction (MLR) at concentrations of $10^{-9}$M (FIG. 15). These neoglycoproteins, which contain multiple copies of a single oligosaccharide, will have wide application in medical research as well as therapeutic applications.

Methods

Synthesis of Neoglycoproteins

1. Preparation of Glycosylamines. Formation of the glycosylamines of 5.8 sugar=Man α3 (Man α6) (Xyl β2) Man β4 GlcNAc, N,N'-diacetylchitobiose, and gentiobiose were performed as follows: One mg each of the three sugar samples was roto-evaporated to dryness and resuspended in 200 μl of saturated ammonium bicarbonate (1M) made up With sterile water. Solid ammonium bicarbonate was then added to maintain saturation of the solution during the incubation period. The tubes were sealed with Parafilm which was then punctured using a needle (to allow the escape of the ammonia and carbon dioxide evolved by decomposition of the salt). After incubation at 30° C. for 3-4 days, the glycosylamine preparations were desalted by direct lyophilization of the reaction mixtures in I ml of distilled water.

2. Preparation of N-Glycyl Derivatives (a) N-chloroacetylation of Glycosylamines. The three glycosylamines were converted to their 1-N-glycyl-β-derivatives via their N-chloroacetamido derivatives using a combination of N-chloroacetylation and ammonolysis. Each of the glycosylamines was dissolved in 100 μl of 1M sodium bicarbonate and cooled on ice. To this was added 5-fold molar excess of solid chloroacetic anhydride, and the reaction mixture was allowed to warm to room temperature. The pH was maintained at or above 7.0 by adding sodium bicarbonate as necessary. Progress of the reaction was monitored by thin layer chromatography (TLC) using acetonitrile/water 7:4 (v/v) and 0.05% diaminobutane as solvent. A total of 3 hr was required to complete the reaction. Following chloroacetylation, the mixture was desalted by passage over a column containing Dowex AG50-X12 (H+) cation exchange resins layered on top of AG3-X4A (OH−) anion exchange resins. The eluant was collected and evaporated to dryness, resuspended in 200 μl of water prior to analysis by $^1$H-NMR and TLC.

(b) Ammonolysis of N-chloroacetylated Glycosylamines. Each of the chloroacetylated mixtures was dissolved in 500 μl of saturated ammonium bicarbonate, sealed in a glass tube to prevent loss of ammonia by evaporation and incubated at 50° C. overnight. The ammonium bicarbonate was then removed by direct lyophilization in 1 ml distilled water.

3. Preparation of N-glycyl Isothiocyanate Derivatives.

The 1-N-glycyl-β-derivative of each of the three sugars was dissolved in 1 ml of 0.1M NaHCO$_3$, pH 8.5, and layered over 1.25 ml of chloroform containing thiophosgene (2.5-fold molar excess). The reaction mixtures were stirred for at least an hour at room temperature in a ventillated fume hood. The reaction mixtures were extracted four times with 1 ml of chloroform. The top aqueous layer after the final spin of the mixtures in an Eppendore centrifuge was carefully removed.

4. Conjugation to Proteins to form Neoglycoproteins

The 1-N-glycyl-β-isothiocyanate derivatives of 5.8 sugar and N,N'-diacetylchitobiose were conjugated to bovine serum albumin, whereas the same derivative of genitobiose was conjugated to human serum albumin. The aqueous layer was added directly to 1 ml of 0.3M NaCl in 0.1M NaHCO$_3$, pH 10, containing varying amount of protein (sugar to protein molar ratios used were 6:1, 10:1, and 5:1/30:1, respectively). The reaction mixtures were stirred overnight at room temperature. Neoglycoproteins were dialyzed against three changes of water and lyophilized. The molar ratios of carbohydrate to protein were determined by the Picotag method as 13, 16, and 25, respectively. N,N'-diacetylchitobiose and 5.8 sugar-bovine serum albumin neoglycoproteins were also analyzed by SDS-polyacrylamide gel electrophoresis and tested for their binding to an anti-GlcNAc antibody and to discoidin (a lectin), respectively (FIG. 16). Gentiobiose-human serum albumin neoglycoprotein was used to inhibit mixed lymphocyte reaction (FIG. 15).

5. Binding of an anti-Glc Antibody to a N,N'-diacetylchitobiose BSA neoglycoprotein immobilized on a Plastic Surface. All procedures were done at room temperature. Serial dilutions of N,N'-diacetylchitobiose-BSA neoglycoprotein (13 sugars/BSA) of each dilution was incubated in a 96 well Falcon plastic ELISA plate for 2 hours (starting concentration of 1.5 mg protein/ml). Unbound neoglycoprotein was rinsed off in PBS. The Falcon plate was then quenched with 4% BSA in PBS for 2 hr. Following several washes in PBS, the plate was incubated with 50 μl of an anti-GlcNAc monoclonal antibody (IgM subclass) solution (1:1000 dilution) for another 2 hours. Unbound antibody was removed by several washings of the plate with PBS. Detection of the anti GlcNAc antibody was performed by incubating the plate with an anti-μ-horseradish peroxidase conjugate (1:500 dilution) for 2 hr. Excess conjugate was removed by several washings in PBS. ELISA was completed by the addition of a substrate for horseradish peroxidase (HRP). Fifty μl of ABTS (12.5 mg/ml) in 0.15M citrate phosphate buffer, pH5.0 was added to each well along with 0.15% H$_2$O$_2$. Color was developed for 15-20 mins. Absorbance at 492–620 nm was read (FIG. 17).

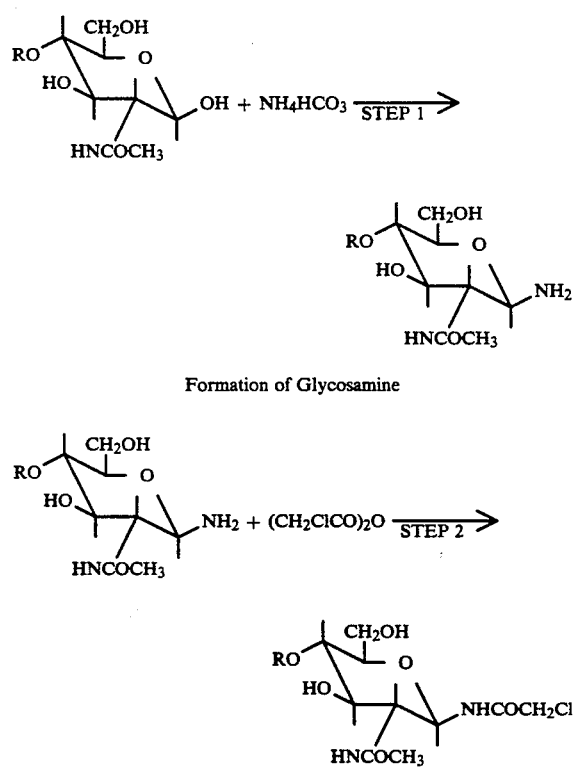

Formation of Glycosamine

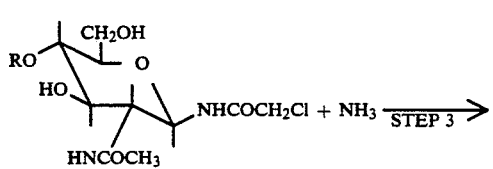

Chloroacetylation

-continued

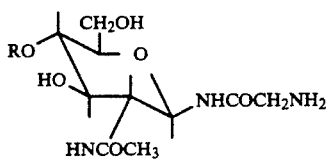

Glycyl derivative

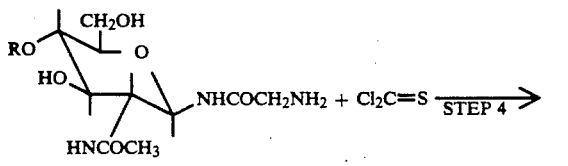

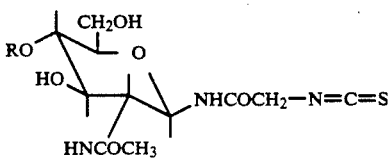

Isothiocyanate derivative

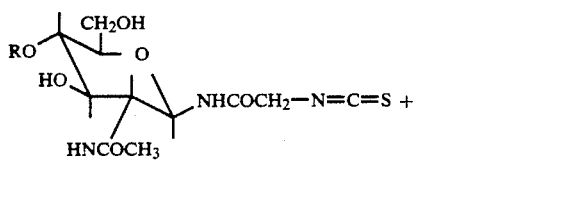

NH₂-Protein $\xrightarrow{\text{STEP 5}}$

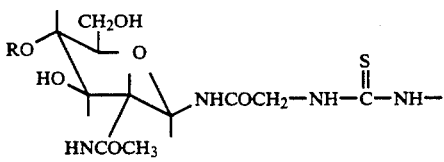

Protein

Scheme for the introduction of a simple spacer function through the formation of the 1-N-chloroacetamido derivative of the glycosylamine (Step 2). This can then be converted to the 1-N-glycyl derivative by ammonolysis (Step 3). The 1-N-glycyl derivative forms the basic intermediate for the formation of oligosaccharide probes.

EXAMPLE 9

Method for the Synthesis of Neoglycolipids

Introduction

Glycolipids are important constituents of all cell-membranes. Like glycoprotein, glycolipids are extemely heterogeneous and difficult to pruify. Glycolipids have been proposed as therapeutic agents in a number of diseases. Their efficacy in treatement of acute spinal cord injuries has been recently demonstrated. In this case, however, a mixture of naturally occurring glycolipids was injected. It would therefore be advantageous to have a method by which glycolipids could be readily synthesized using chemically defined components.

This example illustrates the synthesis of neoglycolipids by coupling the isothiocyanate of the 1-N-β-glycyl derivative of a carbohydrate to either mono or bis octylamine.

Methods

Conjugation to lipids to form Neoglylipids. The isothiocyanate derivative of the 1-N-glycyl-β-glycosylamine of LNFPIII (~0.6 μmole) was conjugated to octylamine (3 μmole) or di-n-octylamine (3 μmole) in CHCl₃:MeOH (1:1). The reaction mixtures were stirred overnight and subsequently dried by rotoevaporation. The dried down mixtures were extracted with CHCl₃:H₂O (1:1) three times to remove unbound sugar derivatives. The CHCl₃ layer was finally dried down by rotoevaporation and resuspended in CHCl₃:MeOH (1:1) for TLC analysis using CHCl₃:MeOH (1:1) as solvent. Both octylamine and di-n-octylamine are ninhydrin sensitive with Rf values of 0.62 and 0.81 respectively. Both neoglycolipids are ninhydrin negative. In contrast, both octylamine and di-n-octylamine are orcinol insensitive whereas the neoglycolipids react. Rfs=0.86 and 0.84 for the LNFPIII-octylamine and LNFPIII-di-n-octylamine neoglycolipids, respectively. The unconjugated LNFPIII is orcinol sensitive and has an Rf value=0.88.

Various other examples will be apparent to the person skilled in the art after reading the present disclosure without departing from the spirit and scope of the appended claims, and it is intended that all such other examples be included within the scope of the appended claims. For example, the claimed N-linked glycoconjugates can be prepared by use of other carriers such as those containing multiple sites (cluster ligands) for conjugation of the isothiocyanate derivatives of the 1-N-glycyl-β-glycosylamines. Illustratively, poly-L-lysine, amino derivatizers, 1,3,5-triazene-2,4,6-triamine, amino derivatives of lipid such as mono- and bis-octylamine and various solid supports are useful carriers. So also, other fluorophores, lipids, peptides, proteins and plastic surfaces can be used in place of the materials specifically illustrated herein with substantially similar results in forming useful N-linked glycoconjugates.

What is claimed is:

1. A process for producing synthetic N-linked glycoconjugates of oligosaccharides under conditions to directly maintain the closed ring structure of the terminal monosaccharide of said oligosaccharides in the β-anomeric configuration comprising reacting an oligosaccharide in saturated ammonium bicarbonate at pH of from about 8 to about 8.5 to form a β-glycosylamine derivative of said oligosaccharide, haloacetylating said β-glycosamine derivative in aqueous phase reaction to directly form the 1-N-haloacetamido derivative of said β-glycosamine derivative without selective crystallization in organic solvent medium, converting said 1-N-haloacetamido derivative to a 1-N-glycyl-β-glycosylamine intermediate derivative by ammonolysis and thereafter reacting said 1-N-glycyl-β-glycosylamine intermediate derivative with a substrate capable of forming a 1-N-glycyl-β-glycosylamine linked glycoconjugate of said substrate and said 1-N-glycyl-β-glycosylamine derivative.

2. The process of claim 1 in which the substrate is selected from the group consisting of a fluorophore, a lipid, a peptide, a protein and a plastic surface.

3. The process of claim 2 in which the substrate is fluorescein isothiocyanate.

4. The process of claim 3 in which a molar excess of the fluorescein isothiocyanate is reacted with the 1-N-glycyl-β-glycosylamine derivative in aqueous NaHCO$_3$ solution.

5. The process of claim 2 in which the substrate is tripalmitoyl-S-glycerylcysteine.

6. The process of claim 5 in which the tripalmitoyl-S-glycerylcysteine is reacted with a molar excess of the 1-N-glycyl-β-glycosylamine derivative in organic solvent medium.

7. The process of claim 2 in which the substrate is an atriopeptin.

8. The process of claim 7 in which the atriopeptin is reacted with the 1-N-glycyl-β-glycosylamine derivative in organic solvent medium.

9. The process of claim 2 in which the substrate is gentiobiose conjugated to serum albumin.

10. The process of claim 9 in which the 1-N-glycyl-β-glycosylamine derivative is reacted with thiophosgene to form an isothiocyanate derivative and thereafter reacted with the gentiobiose conjugated to serum albumin.

11. The process of claim 2 in which the substrate is a polystyrene plastic surface.

12. The process of claim 11 in which the 1-N-glycyl-β-glycosylamine derivative is reacted with thiophosgene to form an isothiocyanate derivative and thereafter reacted with the polystyrene plastic surface.

13. The process of claim 1 in which the haloacetylating step is carried out with a chloroacetylating reagent.

14. The process of claim 13 in which chloroacetylating reagent is chloroacetic anhydride.

15. The process of claim 14 in which at least a 5-fold molar excess of chloroacetic anhydride is used in the haloacetylating step.

16. A process for producing the 1-N-glycyl-β-glycosylamine intermediate derivative of claim 1 under conditions to maintain the β-anomeric configuration comprising reacting an oligosaccharide in saturated ammonium bicarbonate at pH of from about 8 to about 8.5 to form a β-glycosamine derivative of said oligosaccharide, haloacetylating said β-glycosamine derivative in aqueous phase reaction to directly form the 1-N-haloacetamido derivative of said β-glycosamine derivative, and converting said 1-N-haloacetamido derivative to a 1-N-glycyl-β-glycosylamine derivative by ammonolysis.

17. The process of claim 16 in which the haloacetylating step is carried out with a chloroacetylating reagent.

18. The process of claim 17 in which the chloroacetylating reagent is chloroacetic anhydride.

19. The process of claim 18 in which at least a 5-fold molar excess of chloroacetic anhydride is used in the haloacetylating step.

20. A process for producing a synthetic N-linked glycoconjugate of an oligosaccharide and a peptide under conditions to directly maintain the closed ring structure of the terminal monocaccharide of said oligosaccharide in β-anomeric configuration without need for selective crystallization in organic solvent medium comprising reacting an oligosaccharide in saturated ammonium bicarbonate at pH of from about 8 to about 8.5 to form a β-glycosylamine derivative of said oligosaccharide and thereafter reacting said β-glycosylamine derivative with a peptide having an activated carboxyl group capable of forming a β-glycosylamine linked glycoconjugate of said peptide and said β-glycosylamine derivative.

21. The process of claim 20 in which the peptide is an atriopeptin.

* * * * *